United States Patent
Long et al.

(10) Patent No.: US 9,788,885 B2
(45) Date of Patent: *Oct. 17, 2017

(54) ELECTROSURGICAL SYSTEM ENERGY SOURCE

(71) Applicant: Ethicon Endo-Surgery, Inc., Cincinnati, OH (US)

(72) Inventors: Gary L. Long, Cincinnati, OH (US); Gregory J. Bakos, Mason, OH (US); David N. Plescia, Mentor, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/046,917

(22) Filed: Feb. 18, 2016

(65) Prior Publication Data

US 2016/0166311 A1   Jun. 16, 2016

Related U.S. Application Data

(62) Division of application No. 13/586,422, filed on Aug. 15, 2012, now Pat. No. 9,277,957.

(51) Int. Cl.
*A61B 18/00* (2006.01)
*A61B 18/12* (2006.01)
*A61B 18/14* (2006.01)

(52) U.S. Cl.
CPC ...... *A61B 18/1206* (2013.01); *A61B 18/1492* (2013.01); *A61B 2018/00613* (2013.01);
(Continued)

(58) Field of Classification Search
None
See application file for complete search history.

(56) References Cited

U.S. PATENT DOCUMENTS 645,576 A   3/1900   Telsa
649,621 A   5/1900   Tesla
(Continued)

FOREIGN PATENT DOCUMENTS

AU   666310 B2   2/1996
DE   3008120 A1   9/1980
(Continued)

OTHER PUBLICATIONS

Maxim Integrated Application Note 3977: Class D Amplifiers: Fundamentals of Operation and Recent Developments, Jan. 31, 2007.*
(Continued)

*Primary Examiner* — Ankit D Tejani

(57) ABSTRACT

An energy source for use with an electrosurgical system is disclosed. In one embodiment, the energy source includes a power supply, one or more capacitors coupled to the power supply, and a switching component coupled to the one or more capacitors. The switching component is configured to output pulses of a biphasic waveform. The pulses are capable of treating undesired tissue by inducing a change in voltage potential across cell membranes of a plurality of cells in the undesired tissue to promote non-thermal cell death in the plurality of cells. The pulses are also capable of treating the undesired tissue with no or minimal muscle contractions in patient tissue within reach of the biphasic waveform during treatment of the undesired tissue.

24 Claims, 17 Drawing Sheets

(52) U.S. Cl.
CPC .............. *A61B 2018/00791* (2013.01); *A61B 2018/00815* (2013.01); *A61B 2018/00982* (2013.01); *A61B 2018/126* (2013.01)

(56) References Cited

U.S. PATENT DOCUMENTS

| | | | |
|---|---|---|---|
| 787,412 A | 4/1905 | Tesla |
| 1,039,354 A | 9/1912 | Bonadio |
| 1,127,948 A | 2/1915 | Wappler |
| 1,482,653 A | 2/1924 | Lilly |
| 1,581,706 A | 4/1926 | White |
| 1,581,707 A | 4/1926 | White |
| 1,581,708 A | 4/1926 | White |
| 1,581,709 A | 4/1926 | White |
| 1,581,710 A | 4/1926 | White |
| 1,625,602 A | 4/1927 | Gould et al. |
| 1,916,722 A | 7/1933 | Ende |
| 2,028,635 A | 1/1936 | Wappler |
| 2,031,682 A | 2/1936 | Wappler et al. |
| 2,113,246 A | 4/1938 | Wappler |
| 2,137,710 A | 11/1938 | Anderson |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,451,077 A | 10/1948 | Emsig |
| 2,493,108 A | 1/1950 | Casey, Jr. |
| 2,504,152 A | 4/1950 | Riker et al. |
| 2,938,382 A | 5/1960 | De Graaf |
| 2,952,206 A | 9/1960 | Becksted |
| 3,044,461 A | 7/1962 | Murdock |
| 3,069,195 A | 12/1962 | Buck |
| 3,070,088 A | 12/1962 | Brahos |
| 3,170,471 A | 2/1965 | Schnitzer |
| 3,435,824 A | 4/1969 | Gamponia |
| 3,470,876 A | 10/1969 | Barchilon |
| 3,481,325 A | 12/1969 | Glassman |
| 3,595,239 A | 7/1971 | Petersen |
| 3,669,487 A | 6/1972 | Roberts et al. |
| 3,746,881 A | 7/1973 | Fitch et al. |
| 3,799,672 A | 3/1974 | Vurek |
| 3,854,473 A | 12/1974 | Matsuo |
| 3,946,740 A | 3/1976 | Bassett |
| 3,948,251 A | 4/1976 | Hosono |
| 3,961,632 A | 6/1976 | Moossun |
| 3,965,890 A | 6/1976 | Gauthier |
| 3,994,301 A | 11/1976 | Agris |
| 4,011,872 A | 3/1977 | Komiya |
| 4,012,812 A | 3/1977 | Black |
| 4,085,743 A | 4/1978 | Yoon |
| 4,164,225 A | 8/1979 | Johnson et al. |
| 4,170,997 A | 10/1979 | Pinnow et al. |
| 4,174,715 A | 11/1979 | Hasson |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,269,174 A | 5/1981 | Adair |
| 4,278,077 A | 7/1981 | Mizumoto |
| 4,281,646 A | 8/1981 | Kinoshita |
| 4,285,344 A | 8/1981 | Marshall |
| 4,311,143 A | 1/1982 | Komiya |
| 4,329,980 A | 5/1982 | Terada |
| 4,393,872 A | 7/1983 | Reznik et al. |
| 4,396,021 A | 8/1983 | Baumgartner |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,492,232 A | 1/1985 | Green |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,649,904 A | 3/1987 | Krauter et al. |
| 4,653,476 A | 3/1987 | Bonnet |
| 4,655,219 A | 4/1987 | Petruzzi |
| 4,657,016 A | 4/1987 | Garito et al. |
| 4,657,018 A | 4/1987 | Hakky |
| 4,669,470 A | 6/1987 | Brandfield |
| 4,671,477 A | 6/1987 | Cullen |
| 4,677,982 A | 7/1987 | Llinas et al. |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| 4,727,600 A | 2/1988 | Avakian |
| 4,733,662 A | 3/1988 | DeSatnick et al. |
| D295,894 S | 5/1988 | Sharkany et al. |
| 4,742,817 A | 5/1988 | Kawashima et al. |
| 4,753,223 A | 6/1988 | Bremer |
| 4,763,669 A | 8/1988 | Jaeger |
| 4,770,188 A | 9/1988 | Chikama |
| 4,790,624 A | 12/1988 | Van Hoye et al. |
| 4,791,707 A | 12/1988 | Tucker |
| 4,796,627 A | 1/1989 | Tucker |
| 4,807,593 A | 2/1989 | Ito |
| 4,815,450 A | 3/1989 | Patel |
| 4,819,620 A | 4/1989 | Okutsu |
| 4,823,794 A | 4/1989 | Pierce |
| 4,829,999 A | 5/1989 | Auth |
| 4,836,188 A | 6/1989 | Berry |
| 4,846,573 A | 7/1989 | Taylor et al. |
| 4,867,140 A | 9/1989 | Hovis et al. |
| 4,869,238 A | 9/1989 | Opie et al. |
| 4,869,459 A | 9/1989 | Bourne |
| 4,873,979 A | 10/1989 | Hanna |
| 4,880,015 A | 11/1989 | Nierman |
| 4,904,048 A | 2/1990 | Sogawa et al. |
| 4,911,148 A | 3/1990 | Sosnowski et al. |
| 4,926,860 A | 5/1990 | Stice et al. |
| 4,934,364 A | 6/1990 | Green |
| 4,938,214 A | 7/1990 | Specht et al. |
| 4,950,273 A | 8/1990 | Briggs |
| 4,950,285 A | 8/1990 | Wilk |
| 4,953,539 A | 9/1990 | Nakamura et al. |
| 4,960,133 A | 10/1990 | Hewson |
| 4,977,887 A | 12/1990 | Gouda |
| 4,979,496 A | 12/1990 | Komi |
| 4,979,950 A | 12/1990 | Transue et al. |
| 4,984,581 A | 1/1991 | Stice |
| 4,990,152 A | 2/1991 | Yoon |
| 4,991,565 A | 2/1991 | Takahashi et al. |
| 4,994,079 A | 2/1991 | Genese et al. |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,026,379 A | 6/1991 | Yoon |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,098,378 A | 3/1992 | Piontek et al. |
| 5,108,421 A | 4/1992 | Fowler |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,192,300 A | 3/1993 | Fowler |
| 5,197,963 A | 3/1993 | Parins |

(56) References Cited

U.S. PATENT DOCUMENTS

| | | |
|---|---|---|
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,245,460 A | 9/1993 | Allen et al. |
| 5,246,424 A | 9/1993 | Wilk |
| 5,257,999 A | 11/1993 | Slanetz, Jr. |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,275,614 A | 1/1994 | Haber et al. |
| 5,275,616 A | 1/1994 | Fowler |
| 5,284,128 A | 2/1994 | Hart |
| 5,284,162 A | 2/1994 | Wilk |
| 5,287,845 A | 2/1994 | Faul et al. |
| 5,287,852 A | 2/1994 | Arkinstall |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,297,687 A | 3/1994 | Freed |
| 5,301,061 A | 4/1994 | Nakada et al. |
| 5,312,023 A | 5/1994 | Green et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,318,589 A | 6/1994 | Lichtman |
| 5,320,636 A | 6/1994 | Slater |
| 5,324,261 A | 6/1994 | Amundson et al. |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,168 A | 8/1994 | Hemmer |
| 5,334,198 A | 8/1994 | Hart et al. |
| 5,336,192 A | 8/1994 | Palestrant |
| 5,336,222 A | 8/1994 | Durgin, Jr. et al. |
| 5,339,805 A | 8/1994 | Parker |
| 5,341,815 A | 8/1994 | Cofone et al. |
| 5,342,396 A | 8/1994 | Cook |
| 5,344,428 A | 9/1994 | Griffiths |
| 5,345,927 A | 9/1994 | Bonutti |
| 5,348,259 A | 9/1994 | Blanco et al. |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,381 A | 10/1994 | Ensminger et al. |
| 5,356,408 A | 10/1994 | Rydell |
| 5,360,428 A | 11/1994 | Hutchinson, Jr. |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,374,953 A | 12/1994 | Sasaki et al. |
| 5,376,077 A | 12/1994 | Gomringer |
| 5,377,695 A | 1/1995 | An Haack |
| 5,383,877 A | 1/1995 | Clarke |
| 5,383,888 A | 1/1995 | Zvenyatsky et al. |
| 5,386,817 A | 2/1995 | Jones |
| 5,387,259 A | 2/1995 | Davidson |
| 5,391,174 A | 2/1995 | Weston |
| 5,392,789 A | 2/1995 | Slater et al. |
| 5,395,386 A | 3/1995 | Slater |
| 5,397,332 A | 3/1995 | Kammerer et al. |
| 5,401,248 A | 3/1995 | Bencini |
| 5,403,311 A | 4/1995 | Abele et al. |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,431,635 A | 7/1995 | Yoon |
| 5,433,721 A | 7/1995 | Hooven et al. |
| 5,433,735 A | 7/1995 | Zanakis et al. |
| 5,439,471 A | 8/1995 | Kerr |
| 5,439,478 A | 8/1995 | Palmer |
| 5,441,059 A | 8/1995 | Dannan |
| 5,441,494 A | 8/1995 | Ortiz |
| 5,441,498 A | 8/1995 | Perkins |
| 5,441,499 A | 8/1995 | Fritzsch |
| 5,443,463 A | 8/1995 | Stern et al. |
| 5,445,638 A | 8/1995 | Rydell et al. |
| 5,445,648 A | 8/1995 | Cook |
| 5,449,021 A | 9/1995 | Chikama |
| 5,454,827 A | 10/1995 | Aust et al. |
| 5,456,667 A | 10/1995 | Ham et al. |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,472,441 A | 12/1995 | Edwards et al. |
| 5,478,347 A | 12/1995 | Aranyi |
| 5,478,352 A | 12/1995 | Fowler |
| 5,480,404 A | 1/1996 | Kammerer et al. |
| 5,482,029 A | 1/1996 | Sekiguchi et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schülken et al. |
| 5,499,992 A | 3/1996 | Meade et al. |
| 5,499,997 A | 3/1996 | Sharpe et al. |
| 5,500,012 A | 3/1996 | Brucker et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,518,501 A | 5/1996 | Oneda et al. |
| 5,522,829 A | 6/1996 | Michalos |
| 5,522,830 A | 6/1996 | Aranyi |
| 5,527,321 A | 6/1996 | Hinchliffe |
| 5,533,418 A | 7/1996 | Wu et al. |
| 5,536,234 A | 7/1996 | Newman |
| 5,536,248 A | 7/1996 | Weaver et al. |
| 5,538,509 A | 7/1996 | Dunlap et al. |
| 5,540,648 A | 7/1996 | Yoon |
| 5,549,637 A | 8/1996 | Crainich |
| 5,554,151 A | 9/1996 | Hinchliffe |

(56) References Cited

U.S. PATENT DOCUMENTS

| | | |
|---|---|---|
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,571,090 A | 11/1996 | Sherts |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,590,660 A | 1/1997 | MacAulay et al. |
| 5,591,179 A | 1/1997 | Edelstein |
| 5,591,205 A | 1/1997 | Fowler |
| 5,593,420 A | 1/1997 | Eubanks, Jr. et al. |
| 5,595,562 A | 1/1997 | Grier |
| 5,597,378 A | 1/1997 | Jervis |
| 5,601,573 A | 2/1997 | Fogelberg et al. |
| 5,601,574 A | 2/1997 | Stefanchik et al. |
| 5,601,588 A | 2/1997 | Tonomura et al. |
| 5,601,602 A | 2/1997 | Fowler |
| 5,604,531 A | 2/1997 | Iddan et al. |
| 5,607,386 A | 3/1997 | Flam |
| 5,607,389 A | 3/1997 | Edwards et al. |
| 5,607,406 A | 3/1997 | Hernandez et al. |
| 5,607,450 A | 3/1997 | Zvenyatsky et al. |
| 5,609,601 A | 3/1997 | Kolesa et al. |
| 5,613,975 A | 3/1997 | Christy |
| 5,613,977 A | 3/1997 | Weber et al. |
| 5,614,943 A | 3/1997 | Nakamura et al. |
| 5,616,117 A | 4/1997 | Dinkler et al. |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,626,578 A | 5/1997 | Tihon |
| 5,626,587 A | 5/1997 | Bishop et al. |
| 5,628,732 A | 5/1997 | Antoon, Jr. et al. |
| 5,630,782 A | 5/1997 | Adair |
| 5,630,795 A | 5/1997 | Kuramoto et al. |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,645,519 A | 7/1997 | Lee et al. |
| 5,645,565 A | 7/1997 | Rudd et al. |
| 5,649,372 A | 7/1997 | Souza |
| 5,653,677 A | 8/1997 | Okada et al. |
| 5,653,690 A | 8/1997 | Booth et al. |
| 5,653,722 A | 8/1997 | Kieturakis |
| 5,657,755 A | 8/1997 | Desai |
| 5,662,621 A | 9/1997 | Lafontaine |
| 5,662,663 A | 9/1997 | Shallman |
| 5,667,527 A | 9/1997 | Cook |
| 5,669,875 A | 9/1997 | van Eerdenburg |
| 5,681,276 A | 10/1997 | Lundquist |
| 5,681,279 A | 10/1997 | Roper et al. |
| 5,681,324 A | 10/1997 | Kammerer et al. |
| 5,681,330 A | 10/1997 | Hughett et al. |
| 5,685,820 A | 11/1997 | Riek et al. |
| 5,690,606 A | 11/1997 | Slotman |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,711,921 A | 1/1998 | Langford |
| 5,716,326 A | 2/1998 | Dannan |
| 5,716,375 A | 2/1998 | Fowler |
| 5,725,542 A | 3/1998 | Yoon |
| 5,728,094 A | 3/1998 | Edwards |
| 5,730,740 A | 3/1998 | Wales et al. |
| 5,735,849 A | 4/1998 | Baden et al. |
| 5,741,234 A | 4/1998 | Aboul-Hosn |
| 5,741,278 A | 4/1998 | Stevens |
| 5,741,285 A | 4/1998 | McBrayer et al. |
| 5,741,429 A | 4/1998 | Donadio, III et al. |
| 5,743,456 A | 4/1998 | Jones et al. |
| 5,746,759 A | 5/1998 | Meade et al. |
| 5,749,826 A | 5/1998 | Faulkner |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,759,150 A | 6/1998 | Konou et al. |
| 5,759,151 A | 6/1998 | Sturges |
| 5,762,604 A | 6/1998 | Kieturakis |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,776,188 A | 7/1998 | Shepherd et al. |
| 5,779,701 A | 7/1998 | McBrayer et al. |
| 5,779,716 A | 7/1998 | Cano et al. |
| 5,779,720 A | 7/1998 | Walder-Utz et al. |
| 5,779,727 A | 7/1998 | Orejola |
| 5,782,859 A | 7/1998 | Nicholas et al. |
| 5,782,861 A | 7/1998 | Cragg et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,797,959 A | 8/1998 | Castro et al. |
| 5,797,960 A | 8/1998 | Stevens et al. |
| 5,800,449 A | 9/1998 | Wales |
| 5,800,451 A | 9/1998 | Buess et al. |
| 5,803,903 A | 9/1998 | Athas et al. |
| 5,807,395 A | 9/1998 | Mulier et al. |
| 5,808,665 A | 9/1998 | Green |
| 5,810,805 A | 9/1998 | Sutcu et al. |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,026 A | 9/1998 | Yoon |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,818,527 A | 10/1998 | Yamaguchi et al. |
| 5,819,736 A | 10/1998 | Avny et al. |
| 5,823,947 A | 10/1998 | Yoon et al. |
| 5,824,071 A | 10/1998 | Nelson et al. |
| 5,827,190 A | 10/1998 | Palcic et al. |
| 5,827,276 A | 10/1998 | LeVeen et al. |
| 5,827,281 A | 10/1998 | Levin |
| 5,827,299 A | 10/1998 | Thomason et al. |
| 5,827,323 A | 10/1998 | Klieman et al. |
| 5,830,221 A | 11/1998 | Stein et al. |
| 5,830,231 A | 11/1998 | Geiges, Jr. |
| 5,833,603 A | 11/1998 | Kovacs et al. |
| 5,833,700 A | 11/1998 | Fogelberg et al. |
| 5,833,703 A | 11/1998 | Manushakian |
| 5,833,715 A | 11/1998 | Vachon et al. |
| 5,836,960 A | 11/1998 | Kolesa et al. |
| 5,843,017 A | 12/1998 | Yoon |
| 5,843,121 A | 12/1998 | Yoon |
| 5,849,022 A | 12/1998 | Sakashita et al. |
| 5,853,374 A | 12/1998 | Hart et al. |
| 5,855,569 A | 1/1999 | Komi |
| 5,855,585 A | 1/1999 | Kontos |
| 5,860,913 A | 1/1999 | Yamaya et al. |

(56) References Cited

U.S. PATENT DOCUMENTS

| | | |
|---|---|---|
| 5,860,995 A | 1/1999 | Berkelaar |
| 5,868,762 A | 2/1999 | Cragg et al. |
| 5,873,849 A | 2/1999 | Bernard |
| 5,876,411 A | 3/1999 | Kontos |
| 5,882,331 A | 3/1999 | Sasaki |
| 5,882,344 A | 3/1999 | Stouder, Jr. |
| 5,893,846 A | 4/1999 | Bales et al. |
| 5,893,874 A | 4/1999 | Bourque et al. |
| 5,893,875 A | 4/1999 | O'Connor et al. |
| 5,897,487 A | 4/1999 | Ouchi |
| 5,899,919 A | 5/1999 | Eubanks, Jr. et al. |
| 5,902,238 A | 5/1999 | Golden et al. |
| 5,902,254 A | 5/1999 | Magram |
| 5,904,702 A | 5/1999 | Ek et al. |
| 5,906,625 A | 5/1999 | Bito et al. |
| 5,908,420 A | 6/1999 | Parins et al. |
| 5,908,429 A | 6/1999 | Yoon |
| 5,911,737 A | 6/1999 | Lee et al. |
| 5,916,146 A | 6/1999 | Allotta et al. |
| 5,916,147 A | 6/1999 | Boury |
| 5,921,892 A | 7/1999 | Easton |
| 5,921,993 A | 7/1999 | Yoon |
| 5,921,997 A | 7/1999 | Fogelberg et al. |
| 5,922,008 A | 7/1999 | Gimpelson |
| 5,925,052 A | 7/1999 | Simmons |
| 5,928,255 A | 7/1999 | Meade et al. |
| 5,928,266 A | 7/1999 | Kontos |
| 5,936,536 A | 8/1999 | Morris |
| 5,938,661 A | 8/1999 | Hahnen |
| 5,941,815 A | 8/1999 | Chang |
| 5,944,718 A | 8/1999 | Austin et al. |
| 5,951,547 A | 9/1999 | Gough et al. |
| 5,951,549 A | 9/1999 | Richardson et al. |
| 5,954,720 A | 9/1999 | Wilson et al. |
| 5,954,731 A | 9/1999 | Yoon |
| 5,957,936 A | 9/1999 | Yoon et al. |
| 5,957,943 A | 9/1999 | Vaitekunas |
| 5,957,953 A | 9/1999 | DiPoto et al. |
| 5,964,782 A | 10/1999 | Lafontaine et al. |
| 5,970,581 A | 10/1999 | Chadwick et al. |
| 5,971,995 A | 10/1999 | Rousseau |
| 5,972,002 A | 10/1999 | Bark et al. |
| 5,976,074 A | 11/1999 | Moriyama |
| 5,976,075 A | 11/1999 | Beane et al. |
| 5,976,130 A | 11/1999 | McBrayer et al. |
| 5,976,131 A | 11/1999 | Guglielmi et al. |
| 5,980,539 A | 11/1999 | Kontos |
| 5,980,556 A | 11/1999 | Giordano et al. |
| 5,984,938 A | 11/1999 | Yoon |
| 5,984,939 A | 11/1999 | Yoon |
| 5,984,950 A | 11/1999 | Cragg et al. |
| 5,989,182 A | 11/1999 | Hori et al. |
| 5,993,447 A | 11/1999 | Blewett et al. |
| 5,993,474 A | 11/1999 | Ouchi |
| 5,995,875 A | 11/1999 | Blewett et al. |
| 5,997,555 A | 12/1999 | Kontos |
| 6,001,120 A | 12/1999 | Levin |
| 6,004,269 A | 12/1999 | Crowley et al. |
| 6,004,330 A | 12/1999 | Middleman et al. |
| 6,007,566 A | 12/1999 | Wenstrom, Jr. |
| 6,010,515 A | 1/2000 | Swain et al. |
| 6,012,494 A | 1/2000 | Balazs |
| 6,016,452 A | 1/2000 | Kasevich |
| 6,017,356 A | 1/2000 | Frederick et al. |
| 6,019,770 A | 2/2000 | Christoudias |
| 6,024,708 A | 2/2000 | Bales et al. |
| 6,024,747 A | 2/2000 | Kontos |
| 6,027,522 A | 2/2000 | Palmer |
| 6,030,365 A | 2/2000 | Laufer |
| 6,030,384 A | 2/2000 | Nezhat |
| 6,030,634 A | 2/2000 | Wu et al. |
| 6,033,399 A | 3/2000 | Gines |
| 6,033,401 A | 3/2000 | Edwards et al. |
| 6,036,640 A | 3/2000 | Corace et al. |
| 6,036,685 A | 3/2000 | Mueller |
| 6,050,992 A | 4/2000 | Nichols |
| 6,053,927 A | 4/2000 | Hamas |
| 6,053,937 A | 4/2000 | Edwards et al. |
| 6,059,719 A | 5/2000 | Yamamoto et al. |
| 6,066,160 A | 5/2000 | Colvin et al. |
| 6,068,603 A | 5/2000 | Suzuki |
| 6,068,629 A | 5/2000 | Haissaguerre et al. |
| 6,071,233 A | 6/2000 | Ishikawa et al. |
| 6,074,408 A | 6/2000 | Freeman |
| 6,086,530 A | 7/2000 | Mack |
| 6,090,105 A | 7/2000 | Zepeda et al. |
| 6,090,108 A | 7/2000 | McBrayer et al. |
| 6,090,129 A | 7/2000 | Ouchi |
| 6,096,046 A | 8/2000 | Weiss |
| 6,102,909 A | 8/2000 | Chen et al. |
| 6,102,926 A | 8/2000 | Tartaglia et al. |
| 6,106,473 A | 8/2000 | Violante et al. |
| 6,106,521 A | 8/2000 | Blewett et al. |
| 6,109,852 A | 8/2000 | Shahinpoor et al. |
| 6,110,154 A | 8/2000 | Shimomura et al. |
| 6,110,183 A | 8/2000 | Cope |
| 6,113,593 A | 9/2000 | Tu et al. |
| 6,117,144 A | 9/2000 | Nobles et al. |
| 6,117,158 A | 9/2000 | Measamer et al. |
| 6,123,718 A | 9/2000 | Tu et al. |
| 6,131,790 A | 10/2000 | Piraka |
| 6,139,555 A | 10/2000 | Hart et al. |
| 6,141,037 A | 10/2000 | Upton et al. |
| 6,146,391 A | 11/2000 | Cigaina |
| 6,148,222 A | 11/2000 | Ramsey, III |
| 6,149,653 A | 11/2000 | Deslauriers |
| 6,149,662 A | 11/2000 | Pugliesi et al. |
| 6,152,871 A | 11/2000 | Foley et al. |
| 6,152,920 A | 11/2000 | Thompson et al. |
| 6,156,006 A | 12/2000 | Brosens et al. |
| 6,159,200 A | 12/2000 | Verdura et al. |
| 6,165,175 A | 12/2000 | Wampler et al. |
| 6,165,184 A | 12/2000 | Verdura et al. |
| 6,168,570 B1 | 1/2001 | Ferrera |
| 6,168,605 B1 | 1/2001 | Measamer et al. |
| 6,169,269 B1 | 1/2001 | Maynard |
| 6,170,130 B1 | 1/2001 | Hamilton et al. |
| 6,173,872 B1 | 1/2001 | Cohen |
| 6,179,776 B1 | 1/2001 | Adams et al. |
| 6,179,832 B1 | 1/2001 | Jones et al. |
| 6,179,837 B1 | 1/2001 | Hooven |
| 6,183,420 B1 | 2/2001 | Douk et al. |
| 6,190,353 B1 | 2/2001 | Makower et al. |
| 6,190,383 B1 | 2/2001 | Schmaltz et al. |
| 6,190,384 B1 | 2/2001 | Ouchi |
| 6,190,399 B1 | 2/2001 | Palmer et al. |
| 6,203,533 B1 | 3/2001 | Ouchi |
| 6,206,872 B1 | 3/2001 | Lafond et al. |
| 6,206,877 B1 | 3/2001 | Kese et al. |
| 6,206,904 B1 | 3/2001 | Ouchi |
| 6,210,409 B1 | 4/2001 | Ellman et al. |
| 6,214,007 B1 | 4/2001 | Anderson |
| 6,214,028 B1 | 4/2001 | Yoon et al. |
| 6,216,043 B1 | 4/2001 | Swanson et al. |
| 6,228,096 B1 | 5/2001 | Marchand |
| 6,231,506 B1 | 5/2001 | Hu et al. |
| 6,234,958 B1 | 5/2001 | Snoke et al. |
| 6,240,312 B1 | 5/2001 | Alfano et al. |
| 6,245,079 B1 | 6/2001 | Nobles et al. |
| 6,246,914 B1 | 6/2001 | de la Rama et al. |
| 6,258,064 B1 | 7/2001 | Smith et al. |
| 6,261,242 B1 | 7/2001 | Roberts et al. |
| 6,264,664 B1 | 7/2001 | Avellanet |
| 6,270,497 B1 | 8/2001 | Sekino et al. |
| 6,270,505 B1 | 8/2001 | Yoshida et al. |
| 6,277,136 B1 | 8/2001 | Bonutti |
| 6,283,963 B1 | 9/2001 | Regula |
| 6,287,304 B1 | 9/2001 | Eggers et al. |
| 6,293,909 B1 | 9/2001 | Chu et al. |
| 6,293,952 B1 | 9/2001 | Brosens et al. |
| 6,296,630 B1 | 10/2001 | Altman et al. |
| 6,314,963 B1 | 11/2001 | Vaska et al. |
| 6,322,578 B1 | 11/2001 | Houle et al. |
| 6,325,534 B1 | 12/2001 | Hawley et al. |

(56) References Cited

U.S. PATENT DOCUMENTS

| | | |
|---|---|---|
| 6,326,177 B1 | 12/2001 | Schoenbach et al. |
| 6,328,730 B1 | 12/2001 | Harkrider, Jr. |
| 6,350,267 B1 | 2/2002 | Stefanchik |
| 6,350,278 B1 | 2/2002 | Lenker et al. |
| 6,352,503 B1 | 3/2002 | Matsui et al. |
| 6,352,541 B1 | 3/2002 | Kienzle et al. |
| 6,352,543 B1 | 3/2002 | Cole |
| 6,355,013 B1 | 3/2002 | van Muiden |
| 6,355,035 B1 | 3/2002 | Manushakian |
| 6,361,534 B1 | 3/2002 | Chen et al. |
| 6,364,879 B1 | 4/2002 | Chen et al. |
| 6,368,340 B2 | 4/2002 | Malecki et al. |
| 6,371,956 B1 | 4/2002 | Wilson et al. |
| 6,379,366 B1 | 4/2002 | Fleischman et al. |
| 6,383,195 B1 | 5/2002 | Richard |
| 6,383,197 B1 | 5/2002 | Conlon et al. |
| 6,387,671 B1 | 5/2002 | Rubinsky et al. |
| 6,391,029 B1 | 5/2002 | Hooven et al. |
| 6,398,708 B1 | 6/2002 | Hastings et al. |
| 6,402,735 B1 | 6/2002 | Langevin |
| 6,402,746 B1 | 6/2002 | Whayne et al. |
| 6,406,440 B1 | 6/2002 | Stefanchik |
| 6,409,727 B1 | 6/2002 | Bales et al. |
| 6,409,733 B1 | 6/2002 | Conlon et al. |
| 6,419,639 B2 | 7/2002 | Walther et al. |
| 6,419,641 B1 | 7/2002 | Mark et al. |
| 6,427,089 B1 | 7/2002 | Knowlton |
| 6,431,500 B1 | 8/2002 | Jacobs et al. |
| 6,436,107 B1 | 8/2002 | Wang et al. |
| 6,443,970 B1 | 9/2002 | Schulze et al. |
| 6,443,988 B2 | 9/2002 | Felt et al. |
| 6,447,444 B1 | 9/2002 | Avni et al. |
| 6,447,511 B1 | 9/2002 | Slater |
| 6,447,523 B1 | 9/2002 | Middleman et al. |
| 6,454,783 B1 | 9/2002 | Piskun |
| 6,454,785 B2 | 9/2002 | De Hoyos Garza |
| 6,458,074 B1 | 10/2002 | Matsui et al. |
| 6,458,076 B1 | 10/2002 | Pruitt |
| 6,464,701 B1 | 10/2002 | Hooven et al. |
| 6,464,702 B2 | 10/2002 | Schulze et al. |
| 6,470,218 B1 | 10/2002 | Behl |
| 6,475,104 B1 | 11/2002 | Lutz et al. |
| 6,485,411 B1 | 11/2002 | Konstorum et al. |
| 6,489,745 B1 | 12/2002 | Koreis |
| 6,491,626 B1 | 12/2002 | Stone et al. |
| 6,491,627 B1 | 12/2002 | Komi |
| 6,491,691 B1 | 12/2002 | Morley et al. |
| 6,493,590 B1 | 12/2002 | Wessman et al. |
| 6,494,893 B2 | 12/2002 | Dubrul et al. |
| 6,500,176 B1 | 12/2002 | Truckai et al. |
| 6,503,192 B1 | 1/2003 | Ouchi |
| 6,506,190 B1 | 1/2003 | Walshe |
| 6,508,827 B1 | 1/2003 | Manhes |
| 6,514,239 B2 | 2/2003 | Shimmura et al. |
| 6,517,534 B1 | 2/2003 | McGovern et al. |
| 6,520,954 B2 | 2/2003 | Ouchi |
| 6,526,320 B2 | 2/2003 | Mitchell |
| 6,527,782 B2 | 3/2003 | Hogg et al. |
| 6,530,880 B2 | 3/2003 | Pagliuca |
| 6,530,922 B2 | 3/2003 | Cosman et al. |
| 6,535,764 B2 | 3/2003 | Imran et al. |
| 6,537,200 B2 | 3/2003 | Leysieffer et al. |
| 6,543,456 B1 | 4/2003 | Freeman |
| 6,551,270 B1 | 4/2003 | Bimbo et al. |
| 6,551,356 B2 | 4/2003 | Rousseau |
| 6,554,766 B2 | 4/2003 | Maeda et al. |
| 6,554,823 B2 | 4/2003 | Palmer et al. |
| 6,554,829 B2 | 4/2003 | Schulze et al. |
| 6,558,384 B2 | 5/2003 | Mayenberger |
| 6,562,034 B2 | 5/2003 | Edwards et al. |
| 6,562,035 B1 | 5/2003 | Levin |
| 6,562,052 B2 | 5/2003 | Nobles et al. |
| 6,569,120 B1 | 5/2003 | Green et al. |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,579,311 B1 | 6/2003 | Makower |
| 6,581,889 B2 | 6/2003 | Carpenter et al. |
| 6,585,642 B2 | 7/2003 | Christopher |
| 6,585,717 B1 | 7/2003 | Wittenberger et al. |
| 6,587,750 B2 | 7/2003 | Gerbi et al. |
| 6,592,559 B1 | 7/2003 | Pakter et al. |
| 6,592,603 B2 | 7/2003 | Lasner |
| 6,594,971 B1 | 7/2003 | Addy et al. |
| 6,602,262 B2 | 8/2003 | Griego et al. |
| 6,605,105 B1 | 8/2003 | Cuschieri et al. |
| 6,610,072 B1 | 8/2003 | Christy et al. |
| 6,610,074 B2 | 8/2003 | Santilli |
| 6,613,038 B2 | 9/2003 | Bonutti et al. |
| 6,613,068 B2 | 9/2003 | Ouchi |
| 6,616,632 B2 | 9/2003 | Sharp et al. |
| 6,620,193 B1 | 9/2003 | Lau et al. |
| 6,623,448 B2 | 9/2003 | Slater |
| 6,626,919 B1 | 9/2003 | Swanstrom |
| 6,632,171 B2 | 10/2003 | Iddan et al. |
| 6,632,229 B1 | 10/2003 | Yamanouchi |
| 6,632,234 B2 | 10/2003 | Kieturakis et al. |
| 6,638,275 B1 | 10/2003 | McGaffigan et al. |
| 6,638,286 B1 | 10/2003 | Burbank et al. |
| 6,645,225 B1 | 11/2003 | Atkinson |
| 6,652,518 B2 | 11/2003 | Wellman et al. |
| 6,652,521 B2 | 11/2003 | Schulze |
| 6,652,545 B2 | 11/2003 | Shipp et al. |
| 6,652,551 B1 | 11/2003 | Heiss |
| 6,656,194 B1 | 12/2003 | Gannoe et al. |
| 6,663,641 B1 | 12/2003 | Kovac et al. |
| 6,663,655 B2 | 12/2003 | Ginn et al. |
| 6,666,854 B1 | 12/2003 | Lange |
| 6,672,338 B1 | 1/2004 | Esashi et al. |
| 6,673,058 B2 | 1/2004 | Snow |
| 6,673,070 B2 | 1/2004 | Edwards et al. |
| 6,673,087 B1 | 1/2004 | Chang et al. |
| 6,673,092 B1 | 1/2004 | Bacher |
| 6,676,685 B2 | 1/2004 | Pedros et al. |
| 6,679,882 B1 | 1/2004 | Kornerup |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,692,493 B2 | 2/2004 | McGovern et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,188 B2 | 3/2004 | Ushimaru |
| 6,709,445 B2 | 3/2004 | Boebel et al. |
| 6,716,226 B2 | 4/2004 | Sixto, Jr. et al. |
| 6,731,875 B1 | 5/2004 | Kartalopoulos |
| 6,736,822 B2 | 5/2004 | McClellan et al. |
| 6,740,030 B2 | 5/2004 | Martone et al. |
| 6,740,082 B2 | 5/2004 | Shadduck |
| 6,743,166 B2 | 6/2004 | Berci et al. |
| 6,743,226 B2 | 6/2004 | Cosman et al. |
| 6,743,239 B1 | 6/2004 | Kuehn et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,758,857 B2 | 7/2004 | Cioanta et al. |
| 6,761,685 B2 | 7/2004 | Adams et al. |
| 6,761,718 B2 | 7/2004 | Madsen |
| 6,761,722 B2 | 7/2004 | Cole et al. |
| 6,767,356 B2 | 7/2004 | Kanner et al. |
| 6,773,434 B2 | 8/2004 | Ciarrocca |
| 6,776,165 B2 | 8/2004 | Jin |
| 6,776,787 B2 | 8/2004 | Phung et al. |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,382 B1 | 9/2004 | Hoffman |

(56) References Cited

U.S. PATENT DOCUMENTS

| | | |
|---|---|---|
| 6,786,864 B2 | 9/2004 | Matsuura et al. |
| 6,786,905 B2 | 9/2004 | Swanson et al. |
| 6,788,977 B2 | 9/2004 | Fenn et al. |
| 6,790,173 B2 | 9/2004 | Saadat et al. |
| 6,790,217 B2 | 9/2004 | Schulze et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,817,974 B2 | 11/2004 | Cooper et al. |
| 6,818,007 B1 | 11/2004 | Dampney et al. |
| 6,824,548 B2 | 11/2004 | Smith et al. |
| 6,830,545 B2 | 12/2004 | Bendall |
| 6,836,688 B2 | 12/2004 | Ingle et al. |
| 6,837,847 B2 | 1/2005 | Ewers et al. |
| 6,840,246 B2 | 1/2005 | Downing |
| 6,840,938 B1 | 1/2005 | Morley et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,866,628 B2 | 3/2005 | Goodman et al. |
| 6,869,394 B2 | 3/2005 | Ishibiki |
| 6,878,106 B1 | 4/2005 | Herrmann |
| 6,878,110 B2 | 4/2005 | Yang et al. |
| 6,881,213 B2 | 4/2005 | Ryan et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,890,295 B2 | 5/2005 | Michels et al. |
| 6,896,683 B1 | 5/2005 | Gadberry et al. |
| 6,896,692 B2 | 5/2005 | Ginn et al. |
| 6,899,710 B2 | 5/2005 | Hooven |
| 6,908,427 B2 | 6/2005 | Fleener et al. |
| 6,908,476 B2 | 6/2005 | Jud et al. |
| 6,913,613 B2 | 7/2005 | Schwarz et al. |
| 6,916,284 B2 | 7/2005 | Moriyama |
| 6,918,871 B2 | 7/2005 | Schulze |
| 6,918,906 B2 | 7/2005 | Long |
| 6,918,908 B2 | 7/2005 | Bonner et al. |
| 6,926,723 B1 | 8/2005 | Mulhauser et al. |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,932,834 B2 | 8/2005 | Lizardi et al. |
| 6,936,003 B2 | 8/2005 | Iddan |
| 6,939,290 B2 | 9/2005 | Iddan |
| 6,939,292 B2 | 9/2005 | Mizuno |
| 6,939,327 B2 | 9/2005 | Hall et al. |
| 6,942,613 B2 | 9/2005 | Ewers et al. |
| 6,944,490 B1 | 9/2005 | Chow |
| 6,945,472 B2 | 9/2005 | Wuttke et al. |
| 6,945,979 B2 | 9/2005 | Kortenbach et al. |
| 6,949,096 B2 | 9/2005 | Davison et al. |
| 6,955,641 B2 | 10/2005 | Lubock |
| 6,955,683 B2 | 10/2005 | Bonutti |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,960,183 B2 | 11/2005 | Nicolette |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,980,858 B2 | 12/2005 | Fuimaono et al. |
| 6,984,203 B2 | 1/2006 | Tartaglia et al. |
| 6,984,205 B2 | 1/2006 | Gazdzinski |
| 6,986,738 B2 | 1/2006 | Glukhovsky et al. |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,602 B2 | 1/2006 | Nakazawa et al. |
| 6,991,627 B2 | 1/2006 | Madhani et al. |
| 6,991,631 B2 | 1/2006 | Woloszko et al. |
| 6,994,706 B2 | 2/2006 | Chornenky et al. |
| 6,994,708 B2 | 2/2006 | Manzo |
| 6,997,870 B2 | 2/2006 | Couvillon, Jr. |
| 6,997,931 B2 | 2/2006 | Sauer et al. |
| 7,000,818 B2 | 2/2006 | Shelton, IV et al. |
| 7,001,329 B2 | 2/2006 | Kobayashi et al. |
| 7,001,341 B2 | 2/2006 | Gellman et al. |
| 7,008,375 B2 | 3/2006 | Weisel |
| 7,008,419 B2 | 3/2006 | Shadduck |
| 7,009,634 B2 | 3/2006 | Iddan et al. |
| 7,010,340 B2 | 3/2006 | Scarantino et al. |
| 7,011,669 B2 | 3/2006 | Kimblad |
| 7,018,373 B2 | 3/2006 | Suzuki |
| 7,020,531 B1 | 3/2006 | Colliou et al. |
| 7,025,580 B2 | 4/2006 | Heagy et al. |
| 7,025,721 B2 | 4/2006 | Cohen et al. |
| 7,029,435 B2 | 4/2006 | Nakao |
| 7,029,438 B2 | 4/2006 | Morin et al. |
| 7,029,450 B2 | 4/2006 | Gellman |
| 7,032,600 B2 | 4/2006 | Fukuda et al. |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,454 B2 | 5/2006 | Taylor |
| 7,052,489 B2 | 5/2006 | Griego et al. |
| 7,056,330 B2 | 6/2006 | Gayton |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,559 B2 | 7/2006 | Adams et al. |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,010 B2 | 8/2006 | Ootawara et al. |
| 7,087,071 B2 | 8/2006 | Nicholas et al. |
| 7,088,923 B2 | 8/2006 | Haruyama |
| 7,090,673 B2 | 8/2006 | Dycus et al. |
| 7,090,683 B2 | 8/2006 | Brock et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,696 B2 | 9/2006 | Daniel et al. |
| 7,108,703 B2 | 9/2006 | Danitz et al. |
| 7,112,208 B2 | 9/2006 | Morris et al. |
| 7,115,092 B2 | 10/2006 | Park et al. |
| 7,115,124 B1 | 10/2006 | Xiao |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| 7,130,697 B2 | 10/2006 | Chornenky et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |
| 7,150,655 B2 | 12/2006 | Mastrototaro et al. |
| 7,150,750 B2 | 12/2006 | Damarati |
| 7,152,488 B2 | 12/2006 | Hedrich et al. |
| 7,153,321 B2 | 12/2006 | Andrews |

(56) References Cited

U.S. PATENT DOCUMENTS

| | | |
|---|---|---|
| 7,156,845 B2 | 1/2007 | Mulier et al. |
| 7,160,296 B2 | 1/2007 | Pearson et al. |
| 7,163,525 B2 | 1/2007 | Franer |
| 7,169,104 B2 | 1/2007 | Ueda et al. |
| 7,172,714 B2 | 2/2007 | Jacobson |
| 7,175,591 B2 | 2/2007 | Kaladelfos |
| 7,179,254 B2 | 2/2007 | Pendekanti et al. |
| 7,186,265 B2 | 3/2007 | Sharkawy et al. |
| 7,188,627 B2 | 3/2007 | Nelson et al. |
| 7,195,612 B2 | 3/2007 | Van Sloten et al. |
| 7,195,631 B2 | 3/2007 | Dumbauld |
| 7,204,820 B2 | 4/2007 | Akahoshi |
| 7,207,997 B2 | 4/2007 | Shipp et al. |
| 7,208,005 B2 | 4/2007 | Frecker et al. |
| 7,211,089 B2 | 5/2007 | Kear et al |
| 7,211,092 B2 | 5/2007 | Hughett |
| 7,220,227 B2 | 5/2007 | Sasaki et al. |
| 7,223,271 B2 | 5/2007 | Muramatsu et al. |
| 7,223,272 B2 | 5/2007 | Francere et al. |
| 7,229,438 B2 | 6/2007 | Young |
| 7,232,414 B2 | 6/2007 | Gonzalez |
| 7,232,445 B2 | 6/2007 | Kortenbach et al. |
| 7,235,089 B1 | 6/2007 | McGuckin, Jr. |
| 7,241,290 B2 | 7/2007 | Doyle et al. |
| 7,244,228 B2 | 7/2007 | Lubowski |
| 7,250,027 B2 | 7/2007 | Barry |
| 7,252,660 B2 | 8/2007 | Kunz |
| 7,255,675 B2 | 8/2007 | Gertner et al. |
| 7,261,725 B2 | 8/2007 | Binmoeller |
| 7,270,663 B2 | 9/2007 | Nakao |
| 7,288,075 B2 | 10/2007 | Parihar et al. |
| 7,291,127 B2 | 11/2007 | Eidenschink |
| 7,294,139 B1 | 11/2007 | Gengler |
| 7,301,250 B2 | 11/2007 | Cassel |
| 7,306,597 B2 | 12/2007 | Manzo |
| 7,308,828 B2 | 12/2007 | Hashimoto |
| 7,311,107 B2 | 12/2007 | Harel et al. |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,256 B2 | 2/2008 | Johnson et al. |
| 7,329,257 B2 | 2/2008 | Kanehira et al. |
| 7,329,383 B2 | 2/2008 | Stinson |
| 7,335,220 B2 | 2/2008 | Khosravi et al. |
| 7,341,554 B2 | 3/2008 | Sekine et al. |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,390,324 B2 | 6/2008 | Whalen et al. |
| 7,393,322 B2 | 7/2008 | Wenchell |
| 7,402,162 B2 | 7/2008 | Ouchi |
| 7,404,791 B2 | 7/2008 | Linares et al. |
| 7,410,483 B2 | 8/2008 | Danitz et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,229 B2 | 10/2008 | Wolf |
| 7,435,257 B2 | 10/2008 | Lashinski et al. |
| 7,441,507 B2 | 10/2008 | Teraura et al. |
| 7,442,166 B2 | 10/2008 | Huang et al. |
| 7,452,327 B2 | 11/2008 | Durgin et al. |
| 7,455,208 B2 | 11/2008 | Wales et al. |
| 7,455,675 B2 | 11/2008 | Schur et al. |
| 7,468,066 B2 | 12/2008 | Vargas et al. |
| 7,476,237 B2 | 1/2009 | Taniguchi et al. |
| 7,479,104 B2 | 1/2009 | Lau et al. |
| 7,485,093 B2 | 2/2009 | Glukhovsky |
| 7,488,295 B2 | 2/2009 | Burbank et al. |
| 7,494,499 B2 | 2/2009 | Nagase et al. |
| 7,497,867 B2 | 3/2009 | Lasner et al. |
| 7,498,950 B1 | 3/2009 | Ertas et al. |
| 7,507,200 B2 | 3/2009 | Okada |
| 7,507,239 B2 | 3/2009 | Shadduck |
| 7,510,107 B2 | 3/2009 | Timm et al. |
| 7,511,733 B2 | 3/2009 | Takizawa et al. |
| 7,515,953 B2 | 4/2009 | Madar et al. |
| 7,520,876 B2 | 4/2009 | Ressemann et al. |
| 7,524,281 B2 | 4/2009 | Chu et al. |
| 7,524,302 B2 | 4/2009 | Tower |
| 7,534,228 B2 | 5/2009 | Williams |
| 7,540,872 B2 | 6/2009 | Schechter et al. |
| 7,542,807 B2 | 6/2009 | Bertolero et al. |
| 7,544,203 B2 | 6/2009 | Chin et al. |
| 7,548,040 B2 | 6/2009 | Lee et al. |
| 7,549,564 B2 | 6/2009 | Boudreaux |
| 7,549,991 B2 | 6/2009 | Lu et al. |
| 7,549,998 B2 | 6/2009 | Braun |
| 7,553,278 B2 | 6/2009 | Kucklick |
| 7,553,298 B2 | 6/2009 | Hunt et al. |
| 7,559,452 B2 | 7/2009 | Wales et al. |
| 7,559,887 B2 | 7/2009 | Dannan |
| 7,559,916 B2 | 7/2009 | Smith et al. |
| 7,560,006 B2 | 7/2009 | Rakos et al. |
| 7,561,907 B2 | 7/2009 | Fuimaono et al. |
| 7,561,916 B2 | 7/2009 | Hunt et al. |
| 7,565,201 B2 | 7/2009 | Blackmore et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,591,781 B2 | 9/2009 | Hirata |
| 7,597,229 B2 | 10/2009 | Boudreaux et al. |
| 7,604,150 B2 | 10/2009 | Boudreaux |
| 7,608,083 B2 | 10/2009 | Lee et al. |
| 7,611,479 B2 | 11/2009 | Cragg et al. |
| 7,615,002 B2 | 11/2009 | Rothweiler et al. |
| 7,615,005 B2 | 11/2009 | Stefanchik et al. |
| 7,618,398 B2 | 11/2009 | Holman et al. |
| 7,618,437 B2 | 11/2009 | Nakao |
| 7,621,936 B2 | 11/2009 | Cragg et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,648,519 B2 | 1/2010 | Lee et al. |
| 7,650,742 B2 | 1/2010 | Ushijima |
| 7,651,483 B2 | 1/2010 | Byrum et al. |
| 7,651,509 B2 | 1/2010 | Bojarski et al. |
| 7,653,438 B2 | 1/2010 | Deem et al. |
| 7,654,431 B2 | 2/2010 | Hueil et al. |
| 7,655,004 B2 | 2/2010 | Long |
| 7,662,089 B2 | 2/2010 | Okada et al. |
| 7,666,180 B2 | 2/2010 | Holsten et al. |
| 7,666,203 B2 | 2/2010 | Chanduszko et al. |
| 7,670,282 B2 | 3/2010 | Mathis |
| 7,670,336 B2 | 3/2010 | Young et al. |
| 7,674,259 B2 | 3/2010 | Shadduck |
| 7,678,043 B2 | 3/2010 | Gilad |
| 7,680,543 B2 | 3/2010 | Azure |
| 7,684,599 B2 | 3/2010 | Horn et al. |
| 7,684,851 B2 | 3/2010 | Miyake et al. |
| 7,686,826 B2 | 3/2010 | Lee et al. |
| 7,697,970 B2 | 4/2010 | Uchiyama et al. |
| 7,699,835 B2 | 4/2010 | Lee et al. |
| 7,699,864 B2 | 4/2010 | Kick et al. |
| 7,713,189 B2 | 5/2010 | Hanke |
| 7,713,270 B2 | 5/2010 | Suzuki |
| 7,721,742 B2 | 5/2010 | Kalloo et al. |
| 7,736,374 B2 | 6/2010 | Vaughan et al. |
| 7,744,615 B2 | 6/2010 | Couture |
| 7,749,161 B2 | 7/2010 | Beckman et al. |
| 7,751,866 B2 | 7/2010 | Aoki et al. |
| 7,753,901 B2 | 7/2010 | Piskun et al. |
| 7,753,933 B2 | 7/2010 | Ginn et al. |
| 7,758,577 B2 | 7/2010 | Nobis et al. |
| 7,762,949 B2 | 7/2010 | Nakao |
| 7,762,998 B2 | 7/2010 | Birk et al. |
| 7,763,012 B2 | 7/2010 | Petrick et al. |
| 7,765,010 B2 | 7/2010 | Chornenky et al. |

(56) References Cited

U.S. PATENT DOCUMENTS

| | | |
|---|---|---|
| 7,766,896 B2 | 8/2010 | Kornkven Volk et al. |
| 7,770,584 B2 | 8/2010 | Danek et al. |
| 7,771,416 B2 | 8/2010 | Spivey et al. |
| 7,771,437 B2 | 8/2010 | Hogg et al. |
| 7,776,035 B2 | 8/2010 | Rick et al. |
| 7,780,683 B2 | 8/2010 | Roue et al. |
| 7,780,691 B2 | 8/2010 | Stefanchik |
| 7,784,663 B2 | 8/2010 | Shelton, IV |
| 7,794,409 B2 | 9/2010 | Damarati |
| 7,794,447 B2 | 9/2010 | Dann et al. |
| 7,794,458 B2 | 9/2010 | McIntyre et al. |
| 7,794,475 B2 | 9/2010 | Hess et al. |
| 7,798,386 B2 | 9/2010 | Schall et al. |
| 7,815,565 B2 | 10/2010 | Stefanchik et al. |
| 7,815,566 B2 | 10/2010 | Stefanchik et al. |
| 7,815,659 B2 | 10/2010 | Conlon et al. |
| 7,815,662 B2 | 10/2010 | Spivey et al. |
| 7,819,836 B2 | 10/2010 | Levine et al. |
| 7,828,186 B2 | 11/2010 | Wales |
| 7,833,156 B2 | 11/2010 | Williams et al. |
| 7,833,238 B2 | 11/2010 | Nakao |
| 7,837,615 B2 | 11/2010 | Le et al. |
| 7,842,028 B2 | 11/2010 | Lee |
| 7,842,068 B2 | 11/2010 | Ginn |
| 7,846,171 B2 | 12/2010 | Kullas et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,862,553 B2 | 1/2011 | Ewaschuk |
| 7,867,216 B2 | 1/2011 | Wahr et al. |
| 7,871,371 B2 | 1/2011 | Komiya et al. |
| 7,879,004 B2 | 2/2011 | Seibel et al. |
| 7,883,458 B2 | 2/2011 | Hamel |
| 7,887,530 B2 | 2/2011 | Zemlok et al. |
| 7,887,558 B2 | 2/2011 | Lin et al. |
| 7,892,220 B2 | 2/2011 | Faller et al. |
| 7,896,804 B2 | 3/2011 | Uchimura et al. |
| 7,896,887 B2 | 3/2011 | Rimbaugh et al. |
| 7,905,828 B2 | 3/2011 | Brock et al. |
| 7,909,809 B2 | 3/2011 | Scopton et al. |
| 7,914,513 B2 | 3/2011 | Voorhees, Jr. |
| 7,918,785 B2 | 4/2011 | Okada et al. |
| 7,918,869 B2 | 4/2011 | Saadat et al. |
| 7,922,743 B2 | 4/2011 | Heinrich et al. |
| 7,927,271 B2 | 4/2011 | Dimitriou et al. |
| 7,931,624 B2 | 4/2011 | Smith et al. |
| 7,937,143 B2 | 5/2011 | Demarais et al. |
| 7,945,332 B2 | 5/2011 | Schechter |
| 7,947,000 B2 | 5/2011 | Vargas et al. |
| 7,953,326 B2 | 5/2011 | Farr et al. |
| 7,955,298 B2 | 6/2011 | Carroll et al. |
| 7,959,627 B2 | 6/2011 | Utley et al. |
| 7,959,629 B2 | 6/2011 | Young et al. |
| 7,963,975 B2 | 6/2011 | Criscuolo |
| 7,965,180 B2 | 6/2011 | Koyama |
| 7,967,808 B2 | 6/2011 | Fitzgerald et al. |
| 7,969,473 B2 | 6/2011 | Kotoda |
| 7,972,330 B2 | 7/2011 | Alejandro et al. |
| 7,976,458 B2 | 7/2011 | Stefanchik et al. |
| 7,976,552 B2 | 7/2011 | Suzuki |
| 7,985,239 B2 | 7/2011 | Suzuki |
| 7,988,618 B2 | 8/2011 | Mikkaichi et al. |
| 7,988,685 B2 | 8/2011 | Ziaie et al. |
| 8,021,362 B2 | 9/2011 | Deem et al. |
| 8,029,504 B2 | 10/2011 | Long |
| 8,034,046 B2 | 10/2011 | Eidenschink |
| 8,037,591 B2 | 10/2011 | Spivey et al. |
| 8,048,067 B2 | 11/2011 | Davalos et al. |
| 8,048,108 B2 | 11/2011 | Sibbitt et al. |
| 8,052,699 B1 | 11/2011 | Sherwinter |
| 8,057,510 B2 | 11/2011 | Ginn et al. |
| 8,062,306 B2 | 11/2011 | Nobis et al. |
| 8,062,311 B2 | 11/2011 | Litscher et al. |
| 8,066,632 B2 | 11/2011 | Dario et al. |
| 8,066,702 B2 | 11/2011 | Rittman, Iii et al. |
| 8,070,759 B2 | 12/2011 | Stefanchik et al. |
| 8,070,804 B2 | 12/2011 | Hyde et al. |
| 8,075,572 B2 | 12/2011 | Stefanchik et al. |
| 8,075,587 B2 | 12/2011 | Ginn |
| 8,088,062 B2 | 1/2012 | Zwolinski |
| 8,096,459 B2 | 1/2012 | Ortiz et al. |
| 8,096,941 B2 | 1/2012 | Fowler et al. |
| 8,100,922 B2 | 1/2012 | Griffith |
| 8,109,872 B2 | 2/2012 | Kennedy, II et al. |
| 8,114,072 B2 | 2/2012 | Long et al. |
| 8,114,119 B2 | 2/2012 | Spivey et al. |
| 8,118,821 B2 | 2/2012 | Mouw |
| 8,118,834 B1 | 2/2012 | Goraltchouk et al. |
| 8,131,371 B2 | 3/2012 | Demarals et al. |
| 8,147,424 B2 | 4/2012 | Kassab et al. |
| 8,157,813 B2 | 4/2012 | Ko et al. |
| 8,157,834 B2 | 4/2012 | Conlon |
| 8,172,772 B2 | 5/2012 | Zwolinski et al. |
| 8,182,414 B2 | 5/2012 | Handa et al. |
| 8,187,166 B2 | 5/2012 | Kuth et al. |
| 8,200,334 B1 | 6/2012 | Min et al. |
| 8,206,295 B2 | 6/2012 | Kaul |
| 8,211,125 B2 | 7/2012 | Spivey |
| 8,216,224 B2 | 7/2012 | Morris et al. |
| 8,221,310 B2 | 7/2012 | Saadat et al. |
| 8,221,411 B2 | 7/2012 | Francischelli et al. |
| 8,241,204 B2 | 8/2012 | Spivey |
| 8,251,068 B2 | 8/2012 | Schnell |
| 8,252,057 B2 | 8/2012 | Fox |
| 8,262,563 B2 | 9/2012 | Bakos et al. |
| 8,262,655 B2 | 9/2012 | Ghabrial et al. |
| 8,262,680 B2 | 9/2012 | Swain et al. |
| 8,267,854 B2 | 9/2012 | Asada et al. |
| 8,303,581 B2 | 11/2012 | Arts et al. |
| 8,308,738 B2 | 11/2012 | Nobis et al. |
| 8,317,806 B2 | 11/2012 | Coe et al. |
| 8,317,814 B2 | 11/2012 | Karasawa et al. |
| 8,328,836 B2 | 12/2012 | Conlon et al. |
| 8,337,394 B2 | 12/2012 | Vakharia |
| 8,337,492 B2 | 12/2012 | Kunis et al. |
| 8,343,041 B2 | 1/2013 | Byers et al. |
| 8,353,487 B2 | 1/2013 | Trusty et al. |
| 8,357,170 B2 | 1/2013 | Stefanchik |
| 8,359,093 B2 | 1/2013 | Wariar |
| 8,361,066 B2 | 1/2013 | Long et al. |
| 8,361,112 B2 | 1/2013 | Carroll, II et al. |
| 8,377,057 B2 | 2/2013 | Rick et al. |
| 8,403,926 B2 | 3/2013 | Nobis et al. |
| 8,409,200 B2 | 4/2013 | Holcomb et al. |
| 8,425,505 B2 | 4/2013 | Long |
| 8,430,811 B2 | 4/2013 | Hess et al. |
| 8,449,452 B2 | 5/2013 | Iddan et al. |
| 8,449,538 B2 | 5/2013 | Long |
| 8,454,594 B2 | 6/2013 | Demarais et al. |
| 8,475,359 B2 | 7/2013 | Asada et al. |
| 8,480,657 B2 | 7/2013 | Bakos |
| 8,480,689 B2 | 7/2013 | Spivey et al. |
| 8,485,968 B2 | 7/2013 | Weimer et al. |
| 8,496,574 B2 | 7/2013 | Trusty et al. |
| 8,500,697 B2 | 8/2013 | Kurth et al. |
| 8,506,564 B2 | 8/2013 | Long et al. |
| 8,523,939 B1 | 9/2013 | Hausen |
| 8,529,563 B2 | 9/2013 | Long et al. |
| 8,545,396 B2 | 10/2013 | Cover et al. |
| 8,568,410 B2 | 10/2013 | Vakharia et al. |
| 8,579,897 B2 | 11/2013 | Vakharia et al. |
| 8,608,652 B2 | 12/2013 | Voegele et al. |
| 8,623,011 B2 | 1/2014 | Spivey |
| 8,636,648 B2 | 1/2014 | Gazdzinski |
| 8,636,730 B2 | 1/2014 | Keppel |
| 8,640,940 B2 | 2/2014 | Ohdaira |
| 8,652,150 B2 | 2/2014 | Swain et al. |
| 8,668,686 B2 | 3/2014 | Govari et al. |
| 8,679,003 B2 | 3/2014 | Spivey |
| 8,727,967 B2 | 5/2014 | Weitzner |
| 8,747,401 B2 | 6/2014 | Gonzalez et al. |
| 8,771,173 B2 | 7/2014 | Fonger et al. |
| 8,771,260 B2 | 7/2014 | Conlon et al. |
| 8,828,031 B2 | 9/2014 | Fox et al. |

(56) References Cited

U.S. PATENT DOCUMENTS

| | | |
|---|---|---|
| 8,880,185 B2 | 11/2014 | Hastings et al. |
| 8,888,792 B2 | 11/2014 | Harris et al. |
| 8,906,035 B2 | 12/2014 | Zwolinski et al. |
| 8,911,452 B2 | 12/2014 | Skakoon et al. |
| 8,939,897 B2 | 1/2015 | Nobis |
| 8,986,199 B2 | 3/2015 | Weisenburgh, II et al. |
| 9,005,198 B2 | 4/2015 | Long et al. |
| 9,011,431 B2 | 4/2015 | Long et al. |
| 9,028,483 B2 | 5/2015 | Long et al. |
| 9,049,987 B2 | 6/2015 | Conlon et al. |
| 9,078,662 B2 | 7/2015 | Bakos et al. |
| 9,220,526 B2 | 12/2015 | Conlon |
| 9,226,772 B2 | 1/2016 | Fox |
| 9,233,241 B2 | 1/2016 | Long |
| 9,254,169 B2 | 2/2016 | Long et al. |
| 9,271,796 B2 | 3/2016 | Buysse et al. |
| 9,277,957 B2 | 3/2016 | Long et al. |
| 9,314,620 B2 | 4/2016 | Long et al. |
| 9,375,268 B2 | 6/2016 | Long |
| 9,427,255 B2 | 8/2016 | Griffith et al. |
| 2001/0023333 A1 | 9/2001 | Wise et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0029055 A1 | 3/2002 | Bonutti |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0082551 A1 | 6/2002 | Yachia et al. |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0165592 A1 | 11/2002 | Glukhovsky et al. |
| 2002/0173805 A1 | 11/2002 | Matsuno et al. |
| 2002/0183591 A1 | 12/2002 | Matsuura et al. |
| 2003/0014090 A1 | 1/2003 | Abrahamson |
| 2003/0018373 A1 | 1/2003 | Eckhardt et al. |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0078471 A1 | 4/2003 | Foley et al. |
| 2003/0083681 A1 | 5/2003 | Moutafis et al. |
| 2003/0114731 A1 | 6/2003 | Cadeddu et al. |
| 2003/0114732 A1 | 6/2003 | Webler et al. |
| 2003/0120257 A1 | 6/2003 | Houston et al. |
| 2003/0124009 A1 | 7/2003 | Ravi et al. |
| 2003/0130564 A1 | 7/2003 | Martone et al. |
| 2003/0130656 A1 | 7/2003 | Levin |
| 2003/0139646 A1 | 7/2003 | Sharrow et al. |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0187351 A1 | 10/2003 | Franck et al. |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0024414 A1 | 2/2004 | Downing |
| 2004/0034369 A1 | 2/2004 | Sauer et al. |
| 2004/0054322 A1 | 3/2004 | Vargas |
| 2004/0095100 A1* | 5/2004 | Thompson ......... A61B 18/1206 322/32 |
| 2004/0098007 A1 | 5/2004 | Heiss |
| 2004/0101456 A1 | 5/2004 | Kuroshima et al. |
| 2004/0104999 A1 | 6/2004 | Okada |
| 2004/0116948 A1 | 6/2004 | Sixto, Jr. et al. |
| 2004/0127940 A1 | 7/2004 | Ginn et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0161451 A1 | 8/2004 | Pierce et al. |
| 2004/0167545 A1 | 8/2004 | Sadler et al. |
| 2004/0176699 A1 | 9/2004 | Walker et al. |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0199159 A1 | 10/2004 | Lee et al. |
| 2004/0206859 A1 | 10/2004 | Chong et al. |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0225323 A1 | 11/2004 | Nagase et al. |
| 2004/0230095 A1 | 11/2004 | Stefanchik et al. |
| 2004/0230096 A1 | 11/2004 | Stefanchik et al. |
| 2004/0230161 A1 | 11/2004 | Zeiner |
| 2004/0243108 A1 | 12/2004 | Suzuki |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2004/0254572 A1 | 12/2004 | McIntyre et al. |
| 2004/0260198 A1 | 12/2004 | Rothberg et al. |
| 2004/0260315 A1 | 12/2004 | Dell et al. |
| 2004/0260337 A1 | 12/2004 | Freed |
| 2005/0004515 A1 | 1/2005 | Hart et al. |
| 2005/0033265 A1 | 2/2005 | Engel et al. |
| 2005/0033277 A1 | 2/2005 | Clague et al. |
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0059963 A1 | 3/2005 | Phan et al. |
| 2005/0059964 A1 | 3/2005 | Fitz |
| 2005/0065397 A1 | 3/2005 | Saadat et al. |
| 2005/0065509 A1 | 3/2005 | Coldwell et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0070947 A1 | 3/2005 | Franer et al. |
| 2005/0080413 A1 | 4/2005 | Canady |
| 2005/0080435 A1 | 4/2005 | Smith et al. |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0096502 A1 | 5/2005 | Khalili |
| 2005/0101837 A1 | 5/2005 | Kalloo et al. |
| 2005/0101838 A1 | 5/2005 | Camillocci et al. |
| 2005/0101984 A1 | 5/2005 | Chanduszko et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0119613 A1 | 6/2005 | Moenning et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |

(56) References Cited

U.S. PATENT DOCUMENTS

| | | |
|---|---|---|
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216036 A1 | 9/2005 | Nakao |
| 2005/0216050 A1 | 9/2005 | Sepetka et al. |
| 2005/0228224 A1 | 10/2005 | Okada et al. |
| 2005/0228406 A1 | 10/2005 | Bose |
| 2005/0234297 A1 | 10/2005 | Devierre et al. |
| 2005/0240249 A1 | 10/2005 | Tu et al. |
| 2005/0250983 A1 | 11/2005 | Tremaglio et al. |
| 2005/0250987 A1 | 11/2005 | Ewers et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0274935 A1 | 12/2005 | Nelson |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0015131 A1 | 1/2006 | Kierce et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |
| 2006/0025812 A1 | 2/2006 | Shelton, IV |
| 2006/0025819 A1 | 2/2006 | Nobis et al. |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0058776 A1 | 3/2006 | Bilsbury |
| 2006/0064083 A1 | 3/2006 | Khalaj et al. |
| 2006/0069396 A1 | 3/2006 | Meade et al. |
| 2006/0069424 A1 | 3/2006 | Acosta et al. |
| 2006/0069425 A1 | 3/2006 | Hillis et al. |
| 2006/0069429 A1 | 3/2006 | Spence et al. |
| 2006/0074413 A1 | 4/2006 | Behzadian |
| 2006/0079890 A1 | 4/2006 | Guerra |
| 2006/0089528 A1 | 4/2006 | Tartaglia et al. |
| 2006/0095031 A1 | 5/2006 | Ormsby |
| 2006/0095060 A1 | 5/2006 | Mayenberger et al. |
| 2006/0100687 A1 | 5/2006 | Fahey et al. |
| 2006/0106423 A1 | 5/2006 | Weisel et al. |
| 2006/0111209 A1 | 5/2006 | Hinman et al. |
| 2006/0111210 A1 | 5/2006 | Hinman et al. |
| 2006/0111703 A1 | 5/2006 | Kunis et al. |
| 2006/0111704 A1 | 5/2006 | Brenneman et al. |
| 2006/0129166 A1 | 6/2006 | Lavelle |
| 2006/0135962 A1 | 6/2006 | Kick et al. |
| 2006/0135971 A1 | 6/2006 | Swanstrom et al. |
| 2006/0135984 A1 | 6/2006 | Kramer et al. |
| 2006/0142644 A1 | 6/2006 | Mulac et al. |
| 2006/0142652 A1 | 6/2006 | Keenan |
| 2006/0142790 A1 | 6/2006 | Gertner |
| 2006/0142798 A1 | 6/2006 | Holman et al. |
| 2006/0149129 A1 | 7/2006 | Watts et al. |
| 2006/0149131 A1 | 7/2006 | Or |
| 2006/0149132 A1 | 7/2006 | Iddan |
| 2006/0149135 A1 | 7/2006 | Paz |
| 2006/0161190 A1 | 7/2006 | Gadberry et al. |
| 2006/0167416 A1 | 7/2006 | Mathis et al. |
| 2006/0167482 A1 | 7/2006 | Swain et al. |
| 2006/0178560 A1 | 8/2006 | Saadat et al. |
| 2006/0183975 A1 | 8/2006 | Saadat et al. |
| 2006/0184161 A1 | 8/2006 | Maahs et al. |
| 2006/0189844 A1 | 8/2006 | Tien |
| 2006/0189845 A1 | 8/2006 | Maahs et al. |
| 2006/0190027 A1 | 8/2006 | Downey |
| 2006/0195084 A1 | 8/2006 | Slater |
| 2006/0200005 A1 | 9/2006 | Bjork et al. |
| 2006/0200121 A1 | 9/2006 | Mowery |
| 2006/0200169 A1 | 9/2006 | Sniffin |
| 2006/0200170 A1 | 9/2006 | Aranyi |
| 2006/0200199 A1 | 9/2006 | Bonutti et al. |
| 2006/0217665 A1 | 9/2006 | Prosek |
| 2006/0217697 A1 | 9/2006 | Lau et al. |
| 2006/0217742 A1 | 9/2006 | Messerly et al. |
| 2006/0217743 A1 | 9/2006 | Messerly et al. |
| 2006/0229639 A1 | 10/2006 | Whitfield |
| 2006/0229640 A1 | 10/2006 | Whitfield |
| 2006/0237022 A1 | 10/2006 | Chen et al. |
| 2006/0237023 A1 | 10/2006 | Cox et al. |
| 2006/0241570 A1 | 10/2006 | Wilk |
| 2006/0247500 A1 | 11/2006 | Voegele et al. |
| 2006/0247576 A1 | 11/2006 | Poncet |
| 2006/0247663 A1 | 11/2006 | Schwartz et al. |
| 2006/0247673 A1 | 11/2006 | Voegele et al. |
| 2006/0253004 A1 | 11/2006 | Frisch et al. |
| 2006/0253039 A1 | 11/2006 | McKenna et al. |
| 2006/0258907 A1 | 11/2006 | Stefanchik et al. |
| 2006/0258908 A1 | 11/2006 | Stefanchik et al. |
| 2006/0258910 A1 | 11/2006 | Stefanchik et al. |
| 2006/0258954 A1 | 11/2006 | Timberlake et al. |
| 2006/0258955 A1 | 11/2006 | Hoffman et al. |
| 2006/0259010 A1 | 11/2006 | Stefanchik et al. |
| 2006/0259073 A1 | 11/2006 | Miyamoto et al. |
| 2006/0264752 A1 | 11/2006 | Rubinsky et al. |
| 2006/0264904 A1 | 11/2006 | Kerby et al. |
| 2006/0264930 A1 | 11/2006 | Nishimura |
| 2006/0270902 A1 | 11/2006 | Igarashi et al. |
| 2006/0271042 A1 | 11/2006 | Latterell et al. |
| 2006/0271102 A1 | 11/2006 | Bosshard et al. |
| 2006/0276835 A1 | 12/2006 | Uchida |
| 2006/0281970 A1 | 12/2006 | Stokes et al. |
| 2006/0282106 A1 | 12/2006 | Cole et al. |
| 2006/0285732 A1 | 12/2006 | Horn et al. |
| 2006/0287644 A1 | 12/2006 | Inganas et al. |
| 2006/0287666 A1 | 12/2006 | Saadat et al. |
| 2006/0293626 A1 | 12/2006 | Byrum et al. |
| 2007/0000550 A1 | 1/2007 | Osinski |
| 2007/0002135 A1 | 1/2007 | Glukhovsky |
| 2007/0005019 A1 | 1/2007 | Okishige |
| 2007/0010801 A1 | 1/2007 | Chen et al. |
| 2007/0015965 A1 | 1/2007 | Cox et al. |
| 2007/0027469 A1 | 2/2007 | Smith et al. |
| 2007/0032700 A1 | 2/2007 | Fowler et al. |
| 2007/0032701 A1 | 2/2007 | Fowler et al. |
| 2007/0043261 A1 | 2/2007 | Watanabe et al. |
| 2007/0049800 A1 | 3/2007 | Boulais |
| 2007/0049902 A1 | 3/2007 | Griffin et al. |
| 2007/0049968 A1 | 3/2007 | Sibbit et al. |
| 2007/0051375 A1 | 3/2007 | Milliman |
| 2007/0060880 A1 | 3/2007 | Gregorich et al. |
| 2007/0066869 A1 | 3/2007 | Hoffman |
| 2007/0067017 A1 | 3/2007 | Trapp |
| 2007/0073102 A1 | 3/2007 | Matsuno et al. |
| 2007/0073269 A1 | 3/2007 | Becker |
| 2007/0078439 A1 | 4/2007 | Grandt et al. |
| 2007/0079924 A1 | 4/2007 | Saadat et al. |

(56) References Cited

U.S. PATENT DOCUMENTS

| | | |
|---|---|---|
| 2007/0083195 A1 | 4/2007 | Werneth et al. |
| 2007/0088370 A1 | 4/2007 | Kahle et al. |
| 2007/0100375 A1 | 5/2007 | Mikkaichi et al. |
| 2007/0100376 A1 | 5/2007 | Mikkaichi et al. |
| 2007/0106113 A1 | 5/2007 | Ravo |
| 2007/0106118 A1 | 5/2007 | Moriyama |
| 2007/0106317 A1 | 5/2007 | Shelton, IV et al. |
| 2007/0112251 A1 | 5/2007 | Nakhuda |
| 2007/0112331 A1 | 5/2007 | Weber et al. |
| 2007/0112342 A1 | 5/2007 | Pearson et al. |
| 2007/0112383 A1 | 5/2007 | Conlon et al. |
| 2007/0112385 A1 | 5/2007 | Conlon |
| 2007/0112417 A1 | 5/2007 | Shanley et al. |
| 2007/0112425 A1 | 5/2007 | Schaller et al. |
| 2007/0118115 A1 | 5/2007 | Artale et al. |
| 2007/0123840 A1 | 5/2007 | Cox |
| 2007/0129605 A1 | 6/2007 | Schaaf |
| 2007/0129719 A1 | 6/2007 | Kendale et al. |
| 2007/0129760 A1 | 6/2007 | Demarais et al. |
| 2007/0135709 A1 | 6/2007 | Rioux et al. |
| 2007/0135803 A1 | 6/2007 | Belson |
| 2007/0142706 A1 | 6/2007 | Matsui et al. |
| 2007/0142710 A1 | 6/2007 | Yokoi et al. |
| 2007/0142779 A1 | 6/2007 | Duane et al. |
| 2007/0142780 A1 | 6/2007 | Van Lue |
| 2007/0154460 A1 | 7/2007 | Kraft et al. |
| 2007/0156028 A1 | 7/2007 | Van Lue et al. |
| 2007/0156116 A1 | 7/2007 | Gonzalez |
| 2007/0156127 A1 | 7/2007 | Rioux et al. |
| 2007/0161855 A1 | 7/2007 | Mikkaichi et al. |
| 2007/0162101 A1 | 7/2007 | Burgermeister et al. |
| 2007/0167901 A1 | 7/2007 | Herrig et al. |
| 2007/0173686 A1 | 7/2007 | Lin et al. |
| 2007/0173691 A1 | 7/2007 | Yokoi et al. |
| 2007/0173869 A1 | 7/2007 | Gannoe et al. |
| 2007/0173870 A2 | 7/2007 | Zacharias |
| 2007/0173872 A1 | 7/2007 | Neuenfeldt |
| 2007/0179525 A1 | 8/2007 | Frecker et al. |
| 2007/0179530 A1 | 8/2007 | Tieu et al. |
| 2007/0191904 A1 | 8/2007 | Libbus et al. |
| 2007/0197865 A1 | 8/2007 | Miyake et al. |
| 2007/0198057 A1 | 8/2007 | Gelbart et al. |
| 2007/0203398 A1 | 8/2007 | Bonadio et al. |
| 2007/0203487 A1 | 8/2007 | Sugita |
| 2007/0208336 A1 | 9/2007 | Kim et al. |
| 2007/0208364 A1 | 9/2007 | Smith et al. |
| 2007/0208407 A1 | 9/2007 | Gerdts et al. |
| 2007/0213754 A1 | 9/2007 | Mikkaichi et al. |
| 2007/0225552 A1 | 9/2007 | Segawa et al. |
| 2007/0225554 A1 | 9/2007 | Maseda et al. |
| 2007/0233040 A1 | 10/2007 | Macnamara et al. |
| 2007/0244356 A1 | 10/2007 | Carrillo, Jr. et al. |
| 2007/0244358 A1 | 10/2007 | Lee |
| 2007/0250038 A1 | 10/2007 | Boulais |
| 2007/0250057 A1 | 10/2007 | Nobis et al. |
| 2007/0255096 A1 | 11/2007 | Stefanchik et al. |
| 2007/0255100 A1 | 11/2007 | Barlow et al. |
| 2007/0255273 A1 | 11/2007 | Fernandez et al. |
| 2007/0255303 A1 | 11/2007 | Bakos et al. |
| 2007/0255306 A1 | 11/2007 | Conlon et al. |
| 2007/0260112 A1 | 11/2007 | Rahmani |
| 2007/0260117 A1 | 11/2007 | Zwolinski et al. |
| 2007/0260121 A1 | 11/2007 | Bakos et al. |
| 2007/0260242 A1 | 11/2007 | Dycus et al. |
| 2007/0260273 A1 | 11/2007 | Cropper et al. |
| 2007/0260302 A1 | 11/2007 | Igaki |
| 2007/0265494 A1 | 11/2007 | Leanna et al. |
| 2007/0270629 A1 | 11/2007 | Charles |
| 2007/0270889 A1 | 11/2007 | Conlon et al. |
| 2007/0270895 A1 | 11/2007 | Nobis et al. |
| 2007/0270907 A1 | 11/2007 | Stokes et al. |
| 2007/0282165 A1 | 12/2007 | Hopkins et al. |
| 2007/0282371 A1 | 12/2007 | Lee et al. |
| 2007/0293727 A1 | 12/2007 | Goldfarb et al. |
| 2007/0299387 A1 | 12/2007 | Williams et al. |
| 2008/0004650 A1 | 1/2008 | George |
| 2008/0015409 A1 | 1/2008 | Barlow et al. |
| 2008/0015413 A1 | 1/2008 | Barlow et al. |
| 2008/0015552 A1 | 1/2008 | Doyle et al. |
| 2008/0021416 A1 | 1/2008 | Arai et al. |
| 2008/0022927 A1 | 1/2008 | Zhang et al. |
| 2008/0027387 A1 | 1/2008 | Grabinsky |
| 2008/0033244 A1 | 2/2008 | Matsui et al. |
| 2008/0033451 A1 | 2/2008 | Rieber et al. |
| 2008/0051629 A1 | 2/2008 | Sugiyama et al. |
| 2008/0051735 A1 | 2/2008 | Measamer et al. |
| 2008/0058586 A1 | 3/2008 | Karpiel |
| 2008/0058854 A1 | 3/2008 | Kieturakis et al. |
| 2008/0065169 A1 | 3/2008 | Colliou et al. |
| 2008/0071264 A1 | 3/2008 | Azure |
| 2008/0086172 A1 | 4/2008 | Martin et al. |
| 2008/0091068 A1 | 4/2008 | Terliuc |
| 2008/0097159 A1 | 4/2008 | Ishiguro |
| 2008/0097472 A1 | 4/2008 | Agmon et al. |
| 2008/0097483 A1 | 4/2008 | Ortiz et al. |
| 2008/0103527 A1 | 5/2008 | Martin et al. |
| 2008/0114384 A1 | 5/2008 | Chang et al. |
| 2008/0119870 A1 | 5/2008 | Williams |
| 2008/0119891 A1 | 5/2008 | Miles et al. |
| 2008/0125765 A1 | 5/2008 | Berenshteyn et al. |
| 2008/0125774 A1 | 5/2008 | Palanker et al. |
| 2008/0125796 A1 | 5/2008 | Graham |
| 2008/0132892 A1 | 6/2008 | Lunsford et al. |
| 2008/0139882 A1 | 6/2008 | Fujimori |
| 2008/0140069 A1 | 6/2008 | Filloux et al. |
| 2008/0140071 A1 | 6/2008 | Vegesna |
| 2008/0147056 A1 | 6/2008 | van der Weide et al. |
| 2008/0150754 A1 | 6/2008 | Quendt |
| 2008/0171907 A1 | 7/2008 | Long et al. |
| 2008/0177135 A1 | 7/2008 | Muyari et al. |
| 2008/0188710 A1 | 8/2008 | Segawa et al. |
| 2008/0188868 A1 | 8/2008 | Weitzner et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200933 A1 | 8/2008 | Bakos et al. |
| 2008/0200934 A1 | 8/2008 | Fox |
| 2008/0208189 A1 | 8/2008 | Van Wyk et al. |
| 2008/0208213 A1 | 8/2008 | Benjamin et al. |
| 2008/0208280 A1 | 8/2008 | Lindenthaler et al. |
| 2008/0214890 A1 | 9/2008 | Motai et al. |
| 2008/0221587 A1 | 9/2008 | Schwartz |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe et al. |
| 2008/0243148 A1 | 10/2008 | Mikkaichi et al. |
| 2008/0243176 A1 | 10/2008 | Weitzner et al. |
| 2008/0249567 A1 | 10/2008 | Kaplan |
| 2008/0255633 A1 | 10/2008 | Behl et al. |
| 2008/0262513 A1 | 10/2008 | Stahler et al. |
| 2008/0262524 A1 | 10/2008 | Bangera et al. |
| 2008/0262540 A1 | 10/2008 | Bangera et al. |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287801 A1 | 11/2008 | Magnin et al. |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0300571 A1 | 12/2008 | LePivert |
| 2008/0306493 A1 | 12/2008 | Shibata et al. |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0005636 A1 | 1/2009 | Pang et al. |
| 2009/0030278 A1 | 1/2009 | Minakuchi |
| 2009/0054728 A1 | 2/2009 | Trusty |
| 2009/0062788 A1 | 3/2009 | Long et al. |
| 2009/0062795 A1 | 3/2009 | Vakharia et al. |

(56) References Cited

U.S. PATENT DOCUMENTS

| | | |
|---|---|---|
| 2009/0069634 A1 | 3/2009 | Larkin |
| 2009/0076499 A1 | 3/2009 | Azure |
| 2009/0078736 A1 | 3/2009 | Van Lue |
| 2009/0082627 A1 | 3/2009 | Karasawa et al. |
| 2009/0082776 A1 | 3/2009 | Cresina |
| 2009/0082779 A1 | 3/2009 | Nakao |
| 2009/0093690 A1 | 4/2009 | Yoshizawa |
| 2009/0112059 A1 | 4/2009 | Nobis |
| 2009/0112063 A1 | 4/2009 | Bakos et al. |
| 2009/0125042 A1 | 5/2009 | Mouw |
| 2009/0131751 A1 | 5/2009 | Spivey et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0143818 A1 | 6/2009 | Faller et al. |
| 2009/0149710 A1 | 6/2009 | Stefanchik et al. |
| 2009/0163770 A1 | 6/2009 | Torrie et al. |
| 2009/0177031 A1 | 7/2009 | Surti et al. |
| 2009/0177219 A1 | 7/2009 | Conlon |
| 2009/0182325 A1 | 7/2009 | Werneth et al. |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198212 A1 | 8/2009 | Timberlake et al. |
| 2009/0198231 A1 | 8/2009 | Esser et al. |
| 2009/0198253 A1 | 8/2009 | Omori |
| 2009/0209990 A1 | 8/2009 | Yates et al. |
| 2009/0210000 A1 | 8/2009 | Sullivan et al. |
| 2009/0216248 A1 | 8/2009 | Uenohara et al. |
| 2009/0221873 A1 | 9/2009 | McGrath |
| 2009/0227999 A1 | 9/2009 | Willis et al. |
| 2009/0228001 A1 | 9/2009 | Pacey |
| 2009/0248055 A1 | 10/2009 | Spivey et al. |
| 2009/0259105 A1 | 10/2009 | Miyano et al. |
| 2009/0269317 A1 | 10/2009 | Davalos |
| 2009/0281559 A1 | 11/2009 | Swain et al. |
| 2009/0287206 A1 | 11/2009 | Jun |
| 2009/0287236 A1 | 11/2009 | Bakos et al. |
| 2009/0292164 A1 | 11/2009 | Yamatani |
| 2009/0292167 A1 | 11/2009 | Kimoto |
| 2009/0306470 A1 | 12/2009 | Karasawa et al. |
| 2009/0322864 A1 | 12/2009 | Karasawa et al. |
| 2009/0326332 A1 | 12/2009 | Carter |
| 2010/0010294 A1 | 1/2010 | Conlon et al. |
| 2010/0010298 A1 | 1/2010 | Bakos et al. |
| 2010/0010303 A1 | 1/2010 | Bakos |
| 2010/0023032 A1 | 1/2010 | Filho |
| 2010/0030211 A1 | 2/2010 | Davalos et al. |
| 2010/0036198 A1 | 2/2010 | Tacchino et al. |
| 2010/0042045 A1 | 2/2010 | Splvey |
| 2010/0048990 A1 | 2/2010 | Bakos |
| 2010/0049223 A1 | 2/2010 | Filho |
| 2010/0056862 A1 | 3/2010 | Bakos |
| 2010/0056864 A1 | 3/2010 | Lee |
| 2010/0076451 A1 | 3/2010 | Zwolinski et al. |
| 2010/0076460 A1 | 3/2010 | Taylor et al. |
| 2010/0081875 A1 | 4/2010 | Fowler et al. |
| 2010/0091128 A1 | 4/2010 | Ogasawara et al. |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0152539 A1 | 6/2010 | Ghabrial et al. |
| 2010/0152725 A1 | 6/2010 | Pearson et al. |
| 2010/0152746 A1 | 6/2010 | Ceniccola et al. |
| 2010/0191050 A1 | 7/2010 | Zwolinski |
| 2010/0191235 A1* | 7/2010 | Moshe ............... A61B 18/1477 606/41 |
| 2010/0191267 A1 | 7/2010 | Fox |
| 2010/0198248 A1 | 8/2010 | Vakharia |
| 2010/0198254 A1 | 8/2010 | Schaeffer |
| 2010/0210906 A1 | 8/2010 | Wendlandt |
| 2010/0217367 A1 | 8/2010 | Belson |
| 2010/0249700 A1 | 9/2010 | Spivey |
| 2010/0256628 A1 | 10/2010 | Pearson et al. |
| 2010/0261994 A1 | 10/2010 | Davalos et al. |
| 2010/0268025 A1 | 10/2010 | Belson |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331758 A1 | 12/2010 | Davalos et al. |
| 2011/0077476 A1 | 3/2011 | Rofougaran |
| 2011/0087224 A1 | 4/2011 | Cadeddu et al. |
| 2011/0087266 A1 | 4/2011 | Conlon et al. |
| 2011/0087267 A1 | 4/2011 | Spivey et al. |
| 2011/0093009 A1 | 4/2011 | Fox |
| 2011/0098694 A1 | 4/2011 | Long |
| 2011/0098704 A1 | 4/2011 | Long et al. |
| 2011/0106221 A1 | 5/2011 | Neal, II et al. |
| 2011/0112434 A1 | 5/2011 | Ghabrial et al. |
| 2011/0112527 A1 | 5/2011 | Hamilton, Jr. et al. |
| 2011/0115891 A1 | 5/2011 | Trusty |
| 2011/0152610 A1 | 6/2011 | Trusty et al. |
| 2011/0152878 A1 | 6/2011 | Trusty et al. |
| 2011/0152888 A1 | 6/2011 | Ho et al. |
| 2011/0152923 A1 | 6/2011 | Fox |
| 2011/0160514 A1 | 6/2011 | Long et al. |
| 2011/0190764 A1 | 8/2011 | Long et al. |
| 2011/0193948 A1 | 8/2011 | Amling et al. |
| 2011/0224665 A1 | 9/2011 | Crosby et al. |
| 2011/0245619 A1 | 10/2011 | Holcomb |
| 2011/0282149 A1 | 11/2011 | Vargas et al. |
| 2011/0284014 A1 | 11/2011 | Cadeddu et al. |
| 2011/0285488 A1 | 11/2011 | Scott et al. |
| 2011/0288543 A1* | 11/2011 | Cheng ............... A61B 18/1233 606/41 |
| 2012/0004502 A1 | 1/2012 | Weitzner et al. |
| 2012/0010610 A1* | 1/2012 | Keppel ............... A61B 18/1206 606/39 |
| 2012/0029335 A1 | 2/2012 | Sudam et al. |
| 2012/0078266 A1 | 3/2012 | Tyson, Jr. |
| 2012/0088965 A1 | 4/2012 | Stokes et al. |
| 2012/0089089 A1 | 4/2012 | Swain et al. |
| 2012/0089093 A1 | 4/2012 | Trusty |
| 2012/0101331 A1 | 4/2012 | Gilad et al. |
| 2012/0101413 A1 | 4/2012 | Beetel et al. |
| 2012/0109122 A1 | 5/2012 | Arena et al. |
| 2012/0116155 A1 | 5/2012 | Trusty |
| 2012/0116266 A1* | 5/2012 | Houser ............ A61B 17/00234 601/2 |
| 2012/0149981 A1 | 6/2012 | Khait et al. |
| 2012/0150172 A1 | 6/2012 | Ortiz et al. |
| 2012/0191075 A1 | 7/2012 | Trusty |
| 2012/0191076 A1 | 7/2012 | Voegele et al. |
| 2012/0191089 A1* | 7/2012 | Gonzalez ........... A61B 18/1485 606/45 |
| 2012/0239082 A1 | 9/2012 | Shelton, IV et al. |
| 2012/0289857 A1 | 11/2012 | Toth et al. |
| 2013/0030430 A1 | 1/2013 | Stewart et al. |
| 2013/0090666 A1 | 4/2013 | Hess et al. |
| 2013/0138091 A1 | 5/2013 | Coe et al. |
| 2013/0158348 A1 | 6/2013 | Nobis et al. |
| 2013/0172672 A1 | 7/2013 | Iddan et al. |
| 2013/0231530 A1 | 9/2013 | Lien et al. |
| 2013/0245356 A1 | 9/2013 | Fernandez et al. |
| 2013/0331646 A1 | 12/2013 | Pell et al. |
| 2013/0331649 A1 | 12/2013 | Khait et al. |
| 2014/0031813 A1 | 1/2014 | Tellio et al. |
| 2014/0039491 A1 | 2/2014 | Bakos et al. |
| 2014/0039492 A1 | 2/2014 | Long |
| 2014/0052216 A1 | 2/2014 | Long et al. |
| 2014/0121678 A1 | 5/2014 | Trusty et al. |
| 2014/0243597 A1 | 8/2014 | Weisenburgh, II et al. |
| 2014/0343360 A1 | 11/2014 | Shohat et al. |
| 2015/0032132 A1 | 1/2015 | Harris et al. |
| 2015/0230858 A1 | 8/2015 | Long et al. |
| 2015/0265335 A1 | 9/2015 | Bakos et al. |
| 2015/0265342 A1 | 9/2015 | Long et al. |
| 2015/0374444 A1 | 12/2015 | Conlon et al. |
| 2016/0074056 A1 | 3/2016 | Conlon |
| 2016/0100879 A1 | 4/2016 | Long |

(56) References Cited

U.S. PATENT DOCUMENTS

| | | |
|---|---|---|
| 2016/0128759 A1 | 5/2016 | Long et al. |
| 2016/0166311 A1 | 6/2016 | Long et al. |

FOREIGN PATENT DOCUMENTS

| | | |
|---|---|---|
| DE | 4323585 A1 | 1/1995 |
| DE | 19713797 A1 | 10/1997 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0499491 A2 | 8/1992 |
| EP | 0589454 A2 | 3/1994 |
| EP | 0464479 B1 | 3/1995 |
| EP | 0529675 B1 | 2/1996 |
| EP | 0773003 A1 | 5/1997 |
| EP | 0621009 B1 | 7/1997 |
| EP | 0724863 B1 | 7/1999 |
| EP | 0760629 B1 | 11/1999 |
| EP | 0818974 B1 | 7/2001 |
| EP | 1281356 A2 | 2/2003 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 0941128 B1 | 10/2004 |
| EP | 1411843 B1 | 10/2004 |
| EP | 1150614 B1 | 11/2004 |
| EP | 1477104 A1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1582138 B1 | 9/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 0723462 B1 | 3/2009 |
| EP | 1769749 B1 | 11/2009 |
| EP | 2135545 A2 | 12/2009 |
| EP | 1493397 B1 | 9/2011 |
| EP | 2659847 A1 | 11/2013 |
| FR | 2731610 A1 | 9/1996 |
| GB | 330629 A | 6/1930 |
| GB | 2335860 A | 10/1999 |
| GB | 2403909 A | 1/2005 |
| GB | 2421190 A | 6/2006 |
| GB | 2443261 A | 4/2008 |
| JP | 56-46674 | 4/1981 |
| JP | 63309252 A | 12/1988 |
| JP | 4038960 A | 2/1992 |
| JP | H 06-269460 A | 9/1994 |
| JP | 8-29699 A | 2/1996 |
| JP | H 9-75365 A | 3/1997 |
| JP | H 10-24049 A | 1/1998 |
| JP | 3007713 B2 | 2/2000 |
| JP | 2000-107197 A | 4/2000 |
| JP | 2000245683 A | 9/2000 |
| JP | 2001-526072 A | 12/2001 |
| JP | 2002-369791 A | 12/2002 |
| JP | 2003-088494 A | 3/2003 |
| JP | 2003-235852 A | 8/2003 |
| JP | 2004-033525 A | 2/2004 |
| JP | 2004-065745 A | 3/2004 |
| JP | 2005-121947 A | 5/2005 |
| JP | 2005-261514 A | 9/2005 |
| JP | 2005-296063 A | 10/2005 |
| JP | 2006-517843 A | 8/2006 |
| JP | 2006297005 A | 11/2006 |
| JP | 2006-343510 A | 12/2006 |
| JP | 2007-20806 A | 2/2007 |
| JP | 2007-125264 A | 5/2007 |
| JP | 2007-516792 A | 6/2007 |
| JP | 2010/503496 A | 2/2010 |
| JP | 2012-515018 A | 7/2012 |
| NL | 1021295 C2 | 2/2004 |
| SU | 194230 | 5/1967 |
| SU | 980703 | 12/1967 |
| WO | WO 84/01707 A1 | 5/1984 |
| WO | WO 86/07543 A1 | 12/1986 |
| WO | WO 92/13494 A1 | 8/1992 |
| WO | WO 93/10850 A1 | 6/1993 |
| WO | WO 93/20760 A1 | 10/1993 |
| WO | WO 93/20765 A1 | 10/1993 |
| WO | WO 94/22383 A1 | 10/1994 |
| WO | WO 95/09666 A1 | 4/1995 |
| WO | WO 96/22056 A1 | 7/1996 |
| WO | WO 96/27331 A1 | 9/1996 |
| WO | WO 96/39946 A1 | 12/1996 |
| WO | WO 97/12557 A1 | 4/1997 |
| WO | WO 98/01080 A1 | 1/1998 |
| WO | WO 99/00060 A1 | 1/1999 |
| WO | WO 99/09919 A1 | 3/1999 |
| WO | WO 99/17661 A1 | 4/1999 |
| WO | WO 99/30622 A2 | 6/1999 |
| WO | WO 00/22996 A1 | 4/2000 |
| WO | WO 00/35358 A1 | 6/2000 |
| WO | WO 00/68665 A1 | 11/2000 |
| WO | WO 01/10319 A1 | 2/2001 |
| WO | WO 01/26708 A1 | 4/2001 |
| WO | WO 01/41627 A2 | 6/2001 |
| WO | WO 01/58360 A2 | 8/2001 |
| WO | WO 02/11621 A2 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/081761 A2 | 10/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/037149 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2005/122866 A1 | 12/2005 |
| WO | WO 2006/007399 A1 | 1/2006 |
| WO | WO 2006/012630 A2 | 2/2006 |
| WO | WO 2006/040109 A1 | 4/2006 |
| WO | WO 2006/041881 A2 | 4/2006 |
| WO | WO 2006/060405 A2 | 6/2006 |

(56) References Cited

FOREIGN PATENT DOCUMENTS

| WO | WO 2006/110733 A2 | 10/2006 | |
|---|---|---|---|
| WO | WO 2006/113216 A2 | 10/2006 | |
| WO | WO 2007/013059 A2 | 2/2007 | |
| WO | WO 2007/014063 A2 | 2/2007 | |
| WO | WO 2007/035537 A2 | 3/2007 | |
| WO | WO 2007/048085 A2 | 4/2007 | |
| WO | WO 2007/063550 A2 | 6/2007 | |
| WO | WO 2007/100067 A1 | 9/2007 | |
| WO | WO 2007/109171 A2 | 9/2007 | |
| WO | WO 2007/135577 A2 | 11/2007 | |
| WO | WO 2007/143200 A2 | 12/2007 | |
| WO | WO 2007/144004 A1 | 12/2007 | |
| WO | WO 2008/005433 A1 | 1/2008 | |
| WO | WO 2008/033356 A2 | 3/2008 | |
| WO | WO 2008/034103 A2 | 3/2008 | |
| WO | WO 2008/041225 A2 | 4/2008 | |
| WO | WO 2008/076337 A1 | 6/2008 | |
| WO | WO 2008/076800 A2 | 6/2008 | |
| WO | WO 2008/079440 A2 | 7/2008 | |
| WO | WO 2008/080062 A2 | 7/2008 | |
| WO | WO 2008/101075 A2 | 8/2008 | |
| WO | WO 2008/101086 A2 | 8/2008 | |
| WO | WO 2008/102154 A2 | 8/2008 | |
| WO | WO 2008/108863 A2 | 9/2008 | |
| WO | WO 2008/151237 A1 | 12/2008 | |
| WO | WO 2009/021030 A1 | 2/2009 | |
| WO | WO 2009/027065 A1 | 3/2009 | |
| WO | WO 2009/029065 A1 | 3/2009 | |
| WO | WO 2009/032623 A2 | 3/2009 | |
| WO | WO 2009/036457 A1 | 3/2009 | |
| WO | WO 2009/121017 A1 | 10/2009 | |
| WO | WO 2009132190 A2 * | 10/2009 | ......... A61B 18/1206 |
| WO | WO 2010/027688 A1 | 3/2010 | |
| WO | WO 2010/056716 A2 | 5/2010 | |
| WO | WO 2010/080974 A1 | 7/2010 | |
| WO | WO 2010/088481 A1 | 8/2010 | |
| WO | WO 2012/031204 A2 | 3/2012 | |
| WO | WO 2012/068505 A1 | 5/2012 | |
| WO | WO 2012/071526 A2 | 5/2012 | |
| WO | WO 2013/044378 A1 | 4/2013 | |

OTHER PUBLICATIONS

International Search Report for PCT/US2013/052244, Jan. 31, 2014 (8 pages).
Written Opinion for PCT/US2013/052244, Jan. 31, 2014 (12 pages).
International Preliminary Report on Patentability for PCT/US2013/052244, Feb. 17, 2015 (13 pages).
Schoenbach et al. "Bacterial Decontamination of Liquids with Pulsed Electric Fields" IEEE Transactions on Dielectrics and Electrical Insulation. vol. 7 No. 5. Oct. 2000, pp. 637-645.
Davalos, et al., "Tissue Ablation with Irreversible Electroporation," Annals of Biomedical Engineering, 33.2 (2005): 223-231.
Michael S. Kavic, M.D., "Natural Orifice Translumenal Endoscopic Surgery: "NOTES"", JSLS, vol. 10, pp. 133-134 (2006).
Ethicon, Inc., "Wound Closure Manual: Chapter 3 (The Surgical Needle)," 15 pages, (1994).
Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
"Z-Offset Technique Used in the Introduction of Trocar During Laparoscopic Surgery," M.S. Hershey NOTES Presentation to EES Notes Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre DE 1826, Séance Du 24 Fevrier 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Intery Radiol, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastamosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis Col Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USGI® EndoSurgical Operating System—g-Prox® Tissue Grasper/Approximation Device; [online] URL: http://www.usgimedical.com/eos/components-gprox.htm—accessed May 30, 2008 (2 pages).
Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.

(56) References Cited

OTHER PUBLICATIONS

Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. (2007), pp. 255-259.
D.B. Nelson, Md et al., "Endoscopic Hemostatic Devices," Gastrointestinal Endoscopy, vol. 54, No. 6, 2001, pp. 833-840.
CRE™ Pulmonary Balloon Dilator; [online] URL: http://www.bostonscientific.com/Device.bsci?page=HCP_Overview &navRelId=1000.1003&method=D . . . , accessed Jul. 18, 2008 (4 pages).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).
D. Wilhelm et al., "An Innovative, Safe and Sterile Sigmoid Access (ISSA) for NOTES," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavčič et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and cathether-delivered therapies for colorectal liver metastases (CRLM)," EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).
Heller et al., "Electrically mediated plasmid DNA delivery to hepatocellular carcinomas in vivo," Gene Therapy, 7, pp. 826-829 (2000).
Widera et al., "Increased DNA Vaccine Delivery and Immunogenicity by Electroporation in Vivo," The Journal of Immunology, 164, pp. 4635-4640 (2000).
Weaver et al., "Theory of electroporation: A review," Bioelectrochemistry and Bioenergetics, 41, pp. 135-160 (1996).
Mulier et al., "Radiofrequency Ablation Versus Resection for Resectable Colorectal Liver Metastases: Time for a Randomized Trial?" Annals of Surgical Oncology, 15(1), pp. 144-157 (2008).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
Guyton et al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).
"Ethicon Endo-Surgery Studies Presented at DDW Demonstrate Potential of Pure Notes Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal NOTES Sleeve Gastrectomy in a Porcine Model Using a Magnetically Anchored Camera and Novel Instrumentation," Abstract submitted along with Poster at Sages Annual Meeting in Phoenix, AZ, Apr. 22, 2009 (1 page).
Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).
OCTO Port Modular Laparoscopy System for Single Incision Access, Jan. 4, 2010; URL http://www.medgadget.com/archives/2010/01/octo_port_modular_laparo . . . ; accessed Jan. 5, 2010 (4 pages).
Hakko Retractors, obtained Aug. 25, 2009 (5 pages).
Zadno et al., "Linear Superelasticity in Cold-Worked NI-TI," Engineering Aspects of Shape Memory Alloys, pp. 414-419 (1990).
How Stuff Works "How Smart Structures Will Work," http://science.howstuffworks.com/engineering/structural/smart-structure1.htm; accessed online Nov. 1, 2011 (3 pages).
Instant Armor: Science Videos—Science News—ScienCentral; http://www.sciencentral.com/articles./view.php3?article_id=218392121; accessed online Nov. 1, 2011 (2 pages).
Stanway, Smart Fluids: Current and Future Developments. Material Science and Technology, 20, pp. 931-939, 2004; accessed online Nov. 1, 2011 at http://www.dynamics.group.shef.ac.uk/smart/smart.htm (7 pages).
Jolly et al., Properties and Applications of Commercial Magnetorheological Fluids. SPIE 5th Annual Int. Symposium on Smart Structures and Materials, 1998 (18 pages).
Rutala et al. "Guideline for Disinfection and Sterilization in Healthcare Facilities, 2008" (available at http://www.cdc.gov/hicpac/Disinfection_Sterilization/13_11sterilizingPractices.html).
Bewlay et al., "Spinning" in ASM Handbook, vol. 14B, Metalworking: Sheet Forming (2006).

\* cited by examiner

US 9,788,885 B2

ELECTROSURGICAL SYSTEM ENERGY SOURCE

CROSS-REFERENCE TO RELATED APPLICATIONS

This application is a divisional application claiming priority under 35 U.S.C. §121 to U.S. patent application Ser. No. 13/586,422, entitled ELECTROSURGICAL DEVICES AND METHODS, filed Aug. 15, 2012, issued Mar. 8, 2016, now U.S. Pat. No. 9,277,957 the entire disclosure of which is hereby incorporated by reference herein.

BACKGROUND

Electrosurgical therapy has been used in medicine for the treatment of undesirable tissue, such as, for example, diseased tissue, cancer, malignant and benign tumors, masses, lesions, and other abnormal tissue growths. Devices, systems, and methods for conventional ablation therapies may include electrical ablation therapies, such as, for example, high temperature thermal therapies including, focused ultrasound ablation, radiofrequency (RF) ablation, and interstitial laser coagulation, chemical therapies in which chemical agents are injected into the undesirable tissue to cause ablation, surgical excision, cryotherapy, radiation, photodynamic therapy, micrographic surgery, topical treatments with 5-fluorouracil, and laser ablation. Conventional electrical ablation therapies may suffer from some of the following limitations: cost, length of recovery, and extraordinary pain inflicted on the patient. In particular, one drawback of conventional electrical ablation therapies may be any permanent damage to healthy tissue surrounding the undesirable tissue due to detrimental thermal effects resulting from exposing the tissue to thermal energy generated by the electrical ablation device. For example, permanent damage to surrounding healthy tissue may occur when using high temperature thermal therapies to expose undesirable tissue to electric potentials sufficient to cause cell necrosis. Accordingly, electrosurgical devices, systems, and methods for the treatment of undesirable tissue having reduced or no detrimental thermal effects to surrounding healthy tissue are desirable.

FIGURES

The novel features of the various embodiments of the invention are set forth with particularity in the appended claims. The various embodiments of the invention, however, both as to organization and methods of operation, together with further objects and advantages thereof, may best be understood by reference to the following description, taken in conjunction with the accompanying drawings as follows.

SUMMARY

Figure 1:
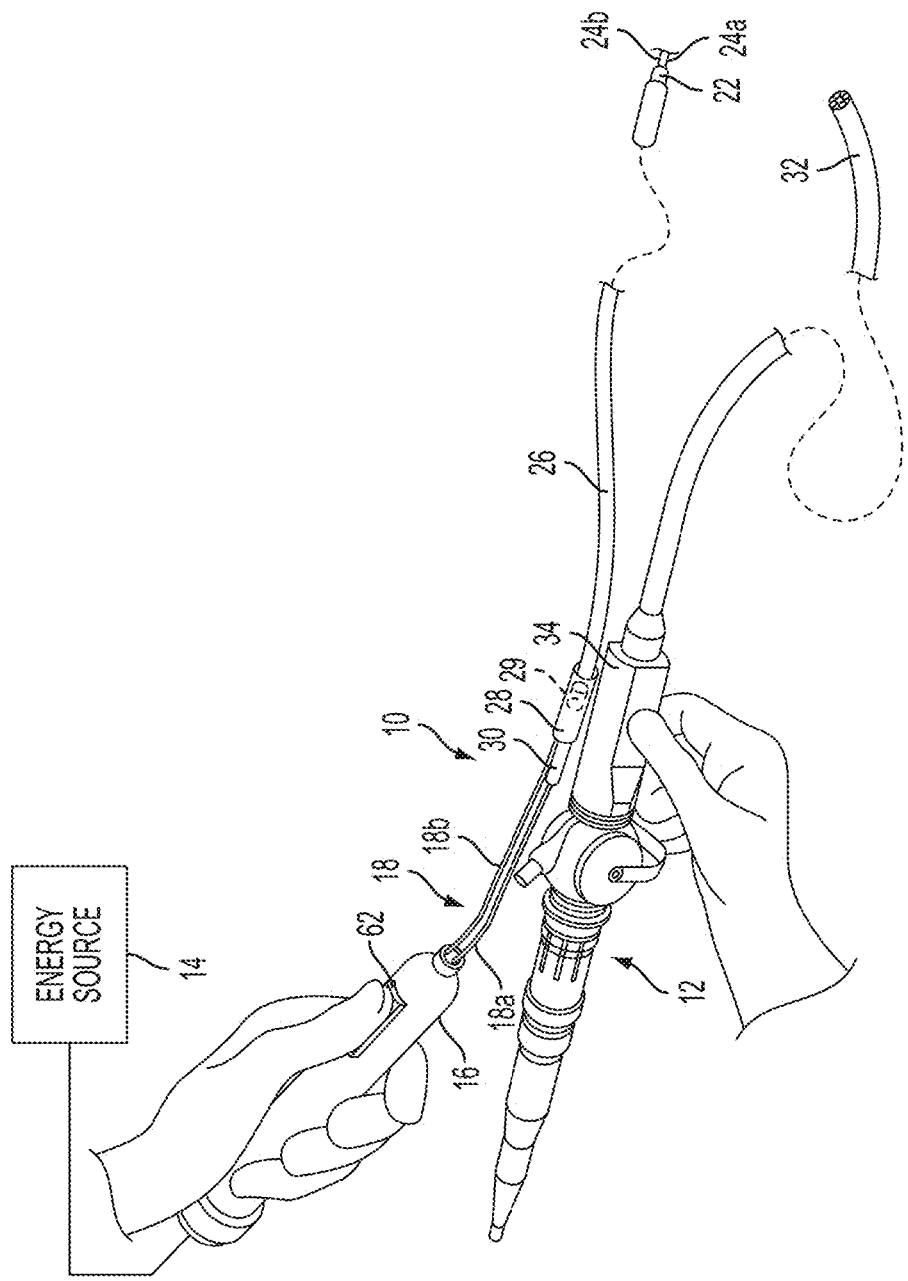
FIG. 1 illustrates an electrosurgical system according to certain embodiments described herein.

In various embodiments, an energy source for use with an electrosurgical system is disclosed. In one embodiment, the energy source comprises a variable voltage power supply, at least one capacitor charged by the variable voltage power supply, and a switching amplifier receiving energy from the at least one capacitor. The switching amplifier is configured to output pulses of a biphasic radio frequency (RF) waveform. The pulses are capable of treating targeted tissue by inducing non-thermal cell death in the targeted tissue.

In various embodiments, an energy source for use with an electrosurgical system is disclosed. In one embodiment, the energy source comprises a variable voltage power supply, a plurality of capacitors electrically coupled to the power supply, and a switching amplifier electrically coupled to the plurality of capacitors. The switching amplifier is configured to output pulses of a biphasic alternating current (AC) waveform. The pulses are operative to treat targeted tissue by inducing a change in voltage potential across cell membranes of the targeted tissue.

In various embodiments, an energy source for use with an electrosurgical system is disclosed. In one embodiment, the energy source comprises a power supply, one or more capacitors coupled to the power supply, and a switching component coupled to the one or more capacitors. The switching component is configured to output pulses of a biphasic waveform. The pulses are capable of treating undesired tissue by inducing a change in voltage potential across cell membranes of a plurality of cells in the undesired tissue to promote non-thermal cell death in the plurality of cells.

DESCRIPTION

Applicant of the present application also owns U.S. patent application Ser. No. 13/586,439, entitled "METHODS FOR PROMOTING WOUND HEALING," filed Aug. 15, 2012, now U.S. Patent Application Publication No. 2014/0052216, the entire disclosure of which is hereby incorporated by reference herein.

Various embodiments are directed to electrosurgical systems, and methods for the treatment of undesirable tissue while having reduced or no detrimental thermal effects to surrounding healthy tissue.

This disclosure describes various elements, features, aspects, and advantages of various embodiments of electrosurgical systems and methods thereof. It is to be understood that certain descriptions of the various embodiments have been simplified to illustrate only those elements, features and aspects that are relevant to a more clear understanding of the disclosed embodiments, while eliminating, for purposes of brevity or clarity, other elements, features and aspects. Any references to "various embodiments," "some embodiments," "one embodiment," or "an embodiment" generally means that a particular element, feature, and/or aspect described in the embodiment is included in at least one embodiment. The phrases "in various embodiments," "in some embodiments," "in one embodiment," or "in an embodiment" may not refer to the same embodiment. Persons having ordinary skill in the art, upon considering the description herein, will recognize that various combinations or sub-combinations of the various embodiments and other elements, features, and aspects may be desirable in particular implementations or applications. However, because such other elements, features, and aspects may be readily ascertained by persons having ordinary skill in the art upon considering the description herein, and are not necessary for a complete understanding of the disclosed embodiments, a description of such elements, features, and aspects may not be provided. As such, it is to be understood that the description set forth herein is merely an illustrative example of the disclosed embodiments and is not intended to limit the scope of the invention as defined solely by the claims.

All numerical quantities stated herein are approximate unless stated otherwise, meaning that the term "about" may be inferred when not expressly stated. The numerical quantities disclosed herein are to be understood as not being strictly limited to the exact numerical values recited. Instead, unless stated otherwise, each numerical value is intended to mean both the recited value and a functionally equivalent range surrounding that value. At the very least, and not as an attempt to limit the application of the doctrine of equivalents to the scope of the claims, each numerical parameter should at least be construed in light of the number of reported significant digits and by applying ordinary rounding techniques. Notwithstanding the approximations of numerical quantities stated herein, the numerical quantities described in specific examples of actual measured values are reported as precisely as possible.

All numerical ranges stated herein include all sub-ranges subsumed therein. For example, a range of "1 to 10" is intended to include all sub-ranges between and including the recited minimum value of 1 and the recited maximum value of 10. Any maximum numerical limitation recited herein is intended to include all lower numerical limitations. Any minimum numerical limitation recited herein is intended to include all higher numerical limitations.

As generally used herein, the terms "proximal" and "distal" generally refer to a clinician manipulating one end of an instrument used to treat a patient. The term "proximal" generally refers to the portion of the instrument closest to the clinician. The term "distal" generally refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

In various embodiments, an electrosurgical system may generally comprise first and second electrodes coupled to an energy source. The energy source may generate and deliver pulses of a biphasic radio frequency (RF) waveform to a patient's tissue. The pulses may non-thermally treat and/or kill cells in undesirable tissue in a patient. The energy source may include an alternating current (AC) electrical waveform generator.

In various embodiments, an electrosurgical system may generally comprise first and second electrodes coupled to an energy source. The energy source may generate and deliver pulses of a biphasic radio frequency (RF) waveform to a patient's tissue. The pulses may induce changes in voltage potential across cell membranes in the tissue. The energy source may include an alternating current (AC) electrical waveform generator.

In various embodiments, an AC waveform generator may be configured to generate and deliver pulses of an AC waveform to a patient's tissue. The AC waveform may be characterized by peak-to-peak voltage amplitude and frequency referred to herein as "fundamental frequency f." The electrical pulses may be characterized by various parameters, such as, for example, frequency, amplitude, pulse width (duration), total number of pulses, and delay between pulses.

In various embodiments, a method of treating undesirable tissue may generally comprise applying pulses of a biphasic RF waveform to the undesirable tissue to non-thermally treat and/or kill cells in the undesirable tissue. In other embodiments, a method of treating undesirable tissue may generally comprise applying pulses of a biphasic radio frequency (RF) waveform to the undesirable tissue to induce change in voltage potential across cell membranes in the undesirable tissue.

In various embodiments, a method of treating undesirable tissue may generally comprise deliver pulses of an AC waveform to a patient's tissue. The AC waveform may be characterized by peak-to-peak voltage amplitude and fundamental frequency f. The electrical pulses may be characterized by various parameters, such as, for example, frequency, amplitude, pulse width (duration), total number of pulses, and delay between pulses.

Without wishing to be bound to any particular theory, cell death in the treated undesirable tissue may occur directly following the treatment. Alternatively, cell death may occur later due to various biological mechanisms. In one theory, cell death may occur due to Irreversible Electroporation (IE). Electroporation, or electropermeabilization, is a significant increase in the electrical conductivity and permeability of the cell plasma membrane caused by an externally applied electrical field. It is usually used in molecular biology as a way of introducing some substance into a cell, such as a molecular probe, a drug that can change the cell's function, or a piece of coding Deoxyribonucleic acid (DNA). Electroporation is a dynamic phenomenon that depends on the local transmembrane voltage at each point on the cell membrane. It is generally accepted that for a given pulse duration and shape, a specific transmembrane voltage threshold exists for the manifestation of the electroporation phenomenon (from 0.5 V to 1 V). Irreversible Electroporation is thought to occur when the transmembrane threshold for a particular cell is surpassed leading to a destabilizing electric potential across cell outer membrane and causing formation of permanent nanoscale defects in the lipid bilayer. The permanent permeabilization of cell membrane leads to changes in cell homeostasis and cell death.

In another theory, cell death may occur due to apoptosis. Apoptosis is programmed cell death. Apoptosis involves a series of biochemical events that lead to a variety of morphological changes, including changes to the cell membrane such as loss of membrane asymmetry and attachment, cell shrinkage, nuclear fragmentation, chromatin condensation, and chromosomal DNA fragmentation.

In various embodiments, an electrosurgical system may generally comprise two or more electrodes configured to be positioned into or proximal to undesirable tissue in a tissue treatment region (e.g., a target site, or a surgical site). The tissue treatment region may have evidence of abnormal tissue growth. In general, the electrodes may comprise an electrically conductive portion (e.g., medical grade stainless steel, gold plated, etc.), and may be configured to electrically couple to an energy source. Once the electrodes are positioned into or proximal to the undesirable tissue, an energizing potential may be applied to the electrodes to create an electric field to which the undesirable tissue is exposed.

Various electrode designs, suitable for use with the present disclosure, described in commonly-owned U.S. Patent Application Publication No. 2009/0182332 A1 titled "IN-LINE ELECTROSURGICAL FORCEPS," filed Jan. 15, 2008, the entire disclosure of which is incorporated herein by reference in its entirety, and commonly-owned U.S. Patent Application Publication No. 2009/0112063 A1 titled "ENDOSCOPIC OVERTUBES," filed Oct. 31, 2007, the entire disclosure of which is incorporated herein by reference in its entirety.

Referring to FIG. 1, an electrosurgical system 10 is illustrated. The electrosurgical system 10 may be employed to treat undesirable tissue, such as, for example, diseased tissue, cancer, malignant and benign tumors, masses, lesions, and other abnormal tissue growths in a tissue treatment region using electrical energy. The electrosurgical system 10 may be configured to treat a number of lesions and ostepathologies comprising metastatic lesions, tumors, fractures, infected sites, and inflamed sites in a tissue treatment region using electrical energy. The electrosurgical system 10 may be configured to be positioned within a patient's natural body orifice, e.g., the mouth, anus, and vagina, and/or advanced through internal body lumen or cavities, e.g., the esophagus, stomach, intestines, colon, cervix, and urethra, to reach the tissue treatment region. The electrosurgical system 10 may be configured to be positioned and passed through a small incision or keyhole formed through the patient's skin or abdominal wall using a trocar to reach the tissue treatment region. The tissue treatment region may be located in the patient's brain, lung, breast, liver, gall bladder, pancreas, prostate gland, various internal body lumen defined by the esophagus, stomach, intestine, colon, arteries, veins, anus, vagina, cervix, fallopian tubes, and the peritoneal cavity. The electrosurgical system 10 may be used in conjunction with endoscopic, laparoscopic, thoracoscopic, open surgical procedures via small incisions or keyholes, percutaneous techniques, transcutaneous techniques, and/or external non-invasive techniques, and any combinations thereof.

Once positioned into or proximate the tissue treatment region, the electrosurgical system 10 may be actuated (e.g., energized) to treat the undesirable tissue. In one embodiment, the electrosurgical system 10 may be configured to treat diseased tissue in the gastrointestinal tract, esophagus, lung, and/or stomach that may be accessed orally. In another embodiment, the electrosurgical system 10 may be adapted to treat undesirable tissue in the liver or other organs that may be accessible using translumenal access techniques, such as, for example, NOTES™ techniques where the electrosurgical systems may be initially introduced through a natural body orifice and then advanced to the tissue treatment site by puncturing the walls of internal body lumen. In various embodiments, the electrosurgical system 10 may be adapted to treat undesirable tissue in the brain, lung, breast, liver, gall bladder, pancreas, or prostate gland, using one or more electrodes positioned percutaneously, transcutaneously, translumenally, minimally invasively, and/or through open surgical techniques, or any combination thereof.

Referring also to FIG. 1, the electrosurgical system 10 may be employed in conjunction with a flexible endoscope 12, as well as a rigid endoscope, laparoscope, or thoracoscope, such as the GIF-100 model available from Olympus Corporation. In one embodiment, the endoscope 12 may be introduced to the tissue treatment region trans-anally through the colon, trans-orally through the esophagus and stomach, trans-vaginally through the cervix, transcutaneously, or via an external incision or keyhole formed in the abdomen in conjunction with a trocar. The electrosurgical system 10 may be inserted and guided into or proximate the tissue treatment region using the endoscope 12. In other embodiments, the endoscope 12 is not utilized, and instead other techniques, such as, for example, ultrasound or a computerized tomography (CT) scan, may be used to determine proper instrument placement during the procedure.

As illustrated in FIG. 1, the endoscope 12 comprises an endoscope handle 34 and an elongate relatively flexible shaft 32. The distal end of the flexible shaft 32 may comprise a light source and a viewing port. Optionally, the flexible shaft 32 may define one or more channels for receiving various instruments therethrough, such as, for example, electrosurgical systems. Images within the field of view of the viewing port may be received by an optical device, such as, for example, a camera comprising a charge coupled device (CCD) usually located within the endoscope 12, and transmitted to a display monitor (not shown) outside the patient. In one embodiment, the electrosurgical system 10 may comprise a plurality of electrical conductors 18, a handpiece 16 comprising an activation switch 62, and an energy source 14, such as, for example, an electrical waveform generator, electrically coupled to the activation switch 62 and the electrosurgical system 10. The electrosurgical system 10 may comprise a relatively flexible member or shaft 22 (FIG. 4) that may be introduced to the tissue treatment region using any of the techniques discussed above, such as, an open incision and a trocar, through one of more of the channels of the endoscope 12, percutaneously, or transcutaneously.

Referring to FIGS. 1-4, one or more electrodes (e.g., needle electrodes, balloon electrodes), such as first and second electrodes 24a,b may extend out from the distal end of the electrosurgical system 10. The first electrode 24a may be configured as the positive electrode and the second electrode 24b may be configured as the negative electrode. The first electrode 24a may be electrically connected to a first electrical conductor 18a, or similar electrically conductive lead or wire, which may be coupled to the positive terminal of the energy source 14 through the activation switch 62. The second electrode 24b may be electrically connected to a second electrical conductor 18b, or similar electrically conductive lead or wire, which may be coupled to the negative terminal of the energy source 14 through the activation switch 62. The electrical conductors 18a,b may be electrically insulated from each other and surrounding structures, except for the electrical connections to the respective electrodes 24a,b.

In certain embodiments, the electrosurgical system 10 may be configured to be introduced into or proximate the tissue treatment region using the endoscope 12 (laparoscope or thoracoscope), open surgical procedures, and/or external and non-invasive medical procedures. The electrodes 24a,b may be referred to herein as endoscopic or laparoscopic electrodes, although variations thereof may be inserted transcutaneously or percutaneously. In various embodiments, one or both electrodes 24a,b may be adapted and configured to slideably move in and out of a cannula, lumen, or channel defined within the flexible shaft 22.

When the electrodes 24a,b are positioned at the desired location into or proximate the tissue treatment region, the electrodes 24a,b may be connected to or disconnected from the energy source 14 by actuating or de-actuating the activation switch 62 on the handpiece 16. The activation switch 62 may be operated manually or may be mounted on a foot switch (not shown), for example. The electrodes 24a,b may deliver electric field pulses to the undesirable tissue. The electric field pulses may be characterized by various parameters, such as, for example, pulse shape, amplitude, frequency, pulse width (duration), and total number of pulses.

Figure 4:
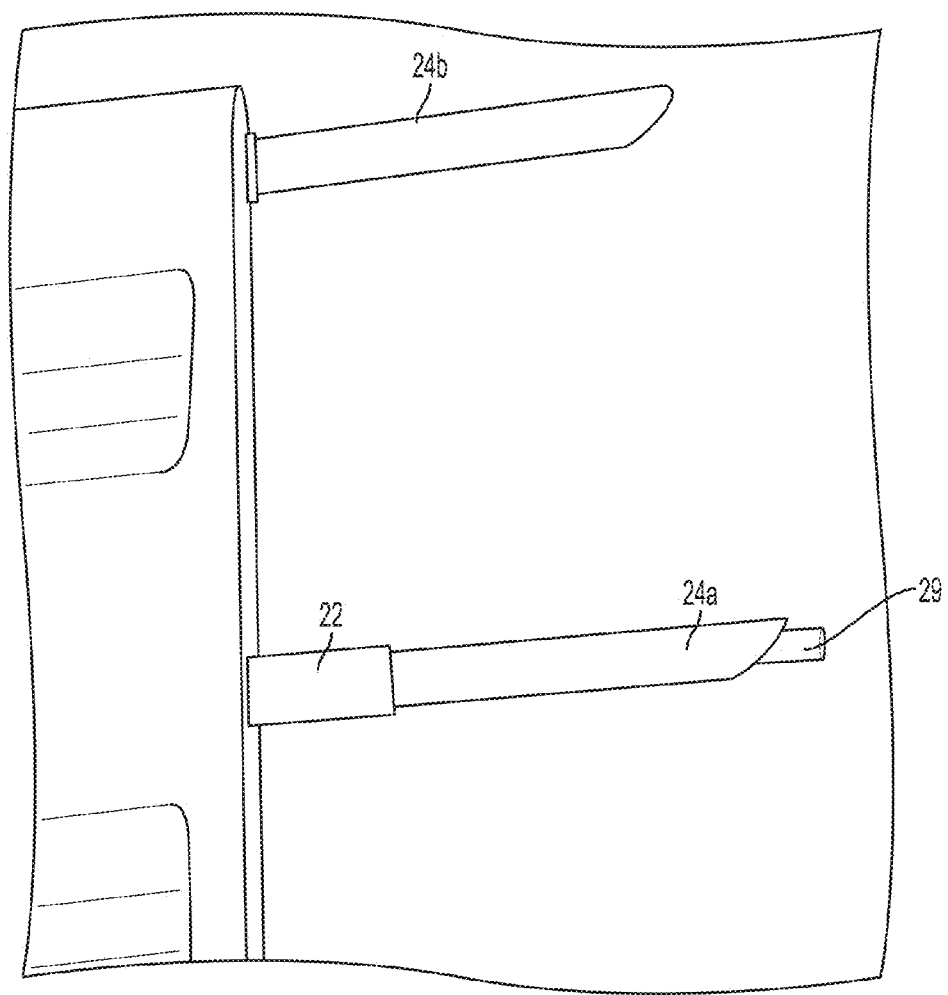
FIG. 4 illustrates at least distal portions of a first electrode and a second electrode of an electrosurgical system including a temperature sensor according to certain embodiments described herein.

Referring to FIG. 4, a protective sleeve or sheath 26 may be slidably disposed over the flexible shaft 22 and within a handle 28. In another embodiment, the sheath 26 may be slidably disposed within the flexible shaft 22 and the handle 28. The sheath 26 may be slidable and may be located over the electrodes 24a,b to protect the trocar and prevent accidental piercing when the electrosurgical system 10 is advanced therethrough. One or both of the electrodes 24a,b may be adapted and configured to slidably move in and out of a cannula, lumen, or channel formed within the flexible shaft 22. One or both of the electrodes 24a,b may be fixed in place. One of the electrodes 24a,b may provide a pivot about which the other electrode may be moved in an arc to other points in the tissue treatment region to treat larger portions of the diseased tissue that cannot be treated by fixing both of the electrodes 24a,b in one location. In one embodiment, one or both of the electrodes 24a,b may be adapted and configured to slidably move in and out of a working channel formed within a flexible shaft 32 of the endoscope 12 or may be located independently of the endoscope 12.

Referring to FIG. 1, the first and second electrical conductors 18a,b may be provided through the handle 28. The first electrode 24a may be slidably moved in and out of the distal end of the flexible shaft 22 using a slide member 30 to retract and/or advance the first electrode 24a. The second electrode 24b may be slidably moved in and out of the distal end of the flexible shaft 22 using the slide member 30 or a different slide member to retract and/or advance the second electrode 24b. One or both electrodes 24a,b may be coupled to the slide member 30, or additional slide members, to advance and retract the electrodes 24a,b and position the electrodes 24a,b. In this manner, the first and second electrodes 24a,b, which may be slidably movable within the cannula, lumen, or channel defined within the flexible shaft 22, may be advanced and retracted with the slide member 30. As shown in FIG. 1, the first electrical conductor 18a coupled to the first electrode 24a may be coupled to the slide member 30. In this manner, the first electrode 24a, which is slidably movable within the cannula, lumen, or channel within the flexible shaft 22, may be advanced and retracted with the slide member 30. In one embodiment, various slide members, such as the slide member 30, may be rotatable. Thus, rotation of the slide member 30 may rotate the corresponding electrode(s) at the distal end of the electrosurgical system 10.

Referring to FIG. 1, transducers or sensors 29 may be located in the handle 28 (or other suitable location) of the electrosurgical system 10 to sense the force with which the electrodes 24a,b penetrate the tissue in the tissue treatment region. This feedback information may be useful to determine whether one or both of the electrodes 24a,b have been properly inserted in the tissue treatment region. As is particularly well known, cancerous tumor tissue tends to be denser than healthy tissue, and thus greater force may be typically required to insert the electrodes 24a,b therein. The transducers or sensors 29 may provide feedback to the operator, surgeon, or clinician to physically sense when the electrodes 24a,b are placed within the cancerous tumor. The feedback information provided by the transducers or sensors 29 may be processed and displayed by circuits located either internally or externally to the energy source 14. The sensor 29 readings may be employed to determine whether the electrodes 24a,b have been properly located within the cancerous tumor thereby assuring that a suitable margin of error has been achieved in locating the electrodes 24a,b. The sensor 29 readings may also be employed to determine whether the pulse parameters need to be adjusted to achieve a desired result, such as, for example, reducing the intensity of muscular contractions in the patient.

Figure 2:
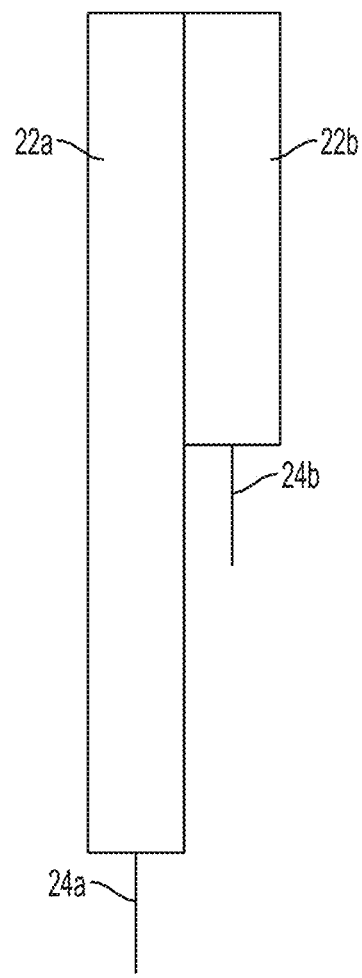
FIG. 2 illustrates at least distal portions of a first electrode and a second electrode of an electrosurgical system according to certain embodiments described herein.

Referring to FIG. 2, the electrosurgical system 10 may comprise a first flexible shaft 22a housing the first electrode 24a and a second flexible shaft 22b housing the second electrode 24b. The electrosurgical system 10 may comprise a first protective sleeve or sheath (not shown) disposed over at least one of the first flexible shaft 22a and second flexible shaft 22b. The electrosurgical system 10 may comprise a first protective sleeve or sheath (not shown) disposed over the first flexible shaft 22a and a second protective sleeve or sheath (not shown) disposed over the second flexible shaft 22b. The length of the first flexible shaft 22a may be different than the length of the second flexible shaft 22b. The length of the first flexible shaft 22a may be greater than or equal to the length of the second flexible shaft 22b. The length of the first protective sleeve or sheath may be different than the length of the second protective sleeve or sheath. The length of the first protective sleeve or sheath may be greater than or equal to the length of the second protective sleeve or sheath.

Figure 3:
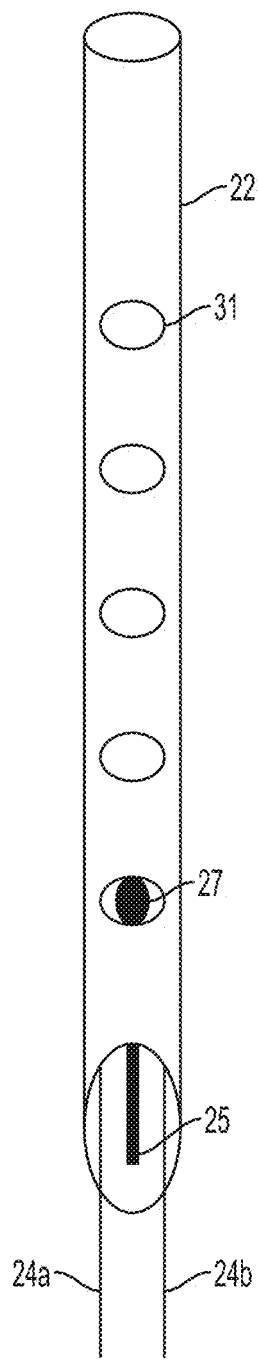
FIG. 3 illustrates at least distal portions of a first electrode and a second electrode of an electrosurgical system including sensors according to certain embodiments described herein.

Referring to FIGS. 1-4, the electrosurgical system 10 may be configured to measure at least one of a temperature and a pressure. The transducers or sensors 29 may comprise at least one of a temperature sensor 25 (FIG. 3) and a pressure sensor 27 (FIG. 3). In certain embodiments, at least one of a temperature sensor 25 and pressure sensor 27 may be located in or proximate the electrosurgical system 10. The temperature sensor 25 and/or pressure sensor 27 may be located within the handle 28. The temperature sensor 25 and/or pressure sensor may be located within the protective sleeve or sheath 26. As shown in the embodiment of FIG. 3, the temperature sensor 25 and/or pressure sensor 27 may be located within the flexible shaft 22. The temperature sensor 25 and/or pressure sensor 27 may be located at the distal end of the flexible shaft 22. The protective sleeve or sheath 26 and/or the flexible shaft 22 may comprise one or more vents 31 configured for measuring at least one of the temperature and pressure of the tissue treatment region. The temperature sensor 25 and/or pressure sensor 27 may be located within the electrodes 24a,b. The pressure sensor 27 may be adjacent to at least one of the vents 31. In one embodiment, the pressure sensor 27 may be adjacent at least one of the vents 31 and the temperature sensor 25 may be located at the distal end of the flexible shaft 22. FIG. 4 is a photograph of an electrosurgical system comprising an optical temperature sensor 29 located within a hollow lumen of the electrode 24a at the distal end of the flexible shaft 22.

In certain embodiments, the temperature sensor and/or pressure sensor may be separate from the electrosurgical system 10. The electrosurgical system 10 may include the temperature sensor 25 and the pressure sensor may be separate from the electrosurgical system 10. The electrosurgical system 10 may include the pressure sensor 27 and the temperature sensor may be separate from the electrosurgical system 10.

According to certain embodiments, the temperature sensor 25 may measure the temperature of the tissue treatment region. The temperature sensor 25 may measure the temperature of the undesirable tissue. The temperature sensor 25 may measure the temperature of the tissue surrounding the electrodes. The temperature sensor 25 may measure the temperature before, during, and/or after treatment.

According to certain embodiments, the pressure sensor 27 may measure the pressure of the tissue treatment region. The pressure sensor 27 may measure the pressure of the space between the electrodes. The pressure sensor 27 may measure the pressure surrounding the electrodes. The pressure sensor 27 may measure the pressure before, during, and/or after treatment.

Without wishing to be bound to any particular theory, electrosurgical system 10 may treat and/or kill cells in undesirable tissue with no or minimal heat applied to the treated tissue, and thus, may not destroy the cellular support structure or regional vasculature. In various embodiments, the temperature of the tissue treated with electrosurgical system 10 may be maintained below or equal to 60° C. In other embodiments, the tissue temperature may be maintained below or equal to 50° C. In yet another embodiment, the tissue temperature may be maintained below or equal to 40° C. The temperature of the tissue may be monitored using the temperature sensor illustrated in FIG. 4.

In one embodiment, the output of the energy source 14 is coupled to the electrodes 24a,b, which may be energized using the activation switch 62 on the handpiece 16, or an activation switch mounted on a foot activated pedal (not shown). Once electrical energy source 14 is coupled to the electrodes 24a,b, an electric field may be formed at a distal end of the electrodes 24a,b.

The electrodes 24a,b may have a diameter or radius from 0.5 mm to 1.5 mm, such as, for example, 0.5 mm, 0.75 mm, 1 mm, and 1.5 mm. In various embodiments, the diameter of the first electrode 24a may by different from the diameter of the second electrode 24b. The electrode spacing may be from 0.5 cm to 3 cm. In various embodiments, the distance from the first electrode 24a to the second electrode 24b may be from 0.5 cm to 3 cm, such as, for example, 1 cm, 1.5 cm, 2.0 cm, and 3 cm. In one embodiment, the electrosurgical system 10 may comprise multiple needle electrodes.

According to certain embodiments, the electrosurgical system 10 may be introduced into the tissue treatment region through a trocar, for example, or inserted to a tissue treatment region transcutaneously, percutaneously, or other suitable techniques. In one embodiment, the cannula, lumen, or channel defined within the flexible shaft 22 may comprise a cutting edge, such as a bevel or other sharp edge, to aid in the puncturing/piercing of tissue.

Figure 5:
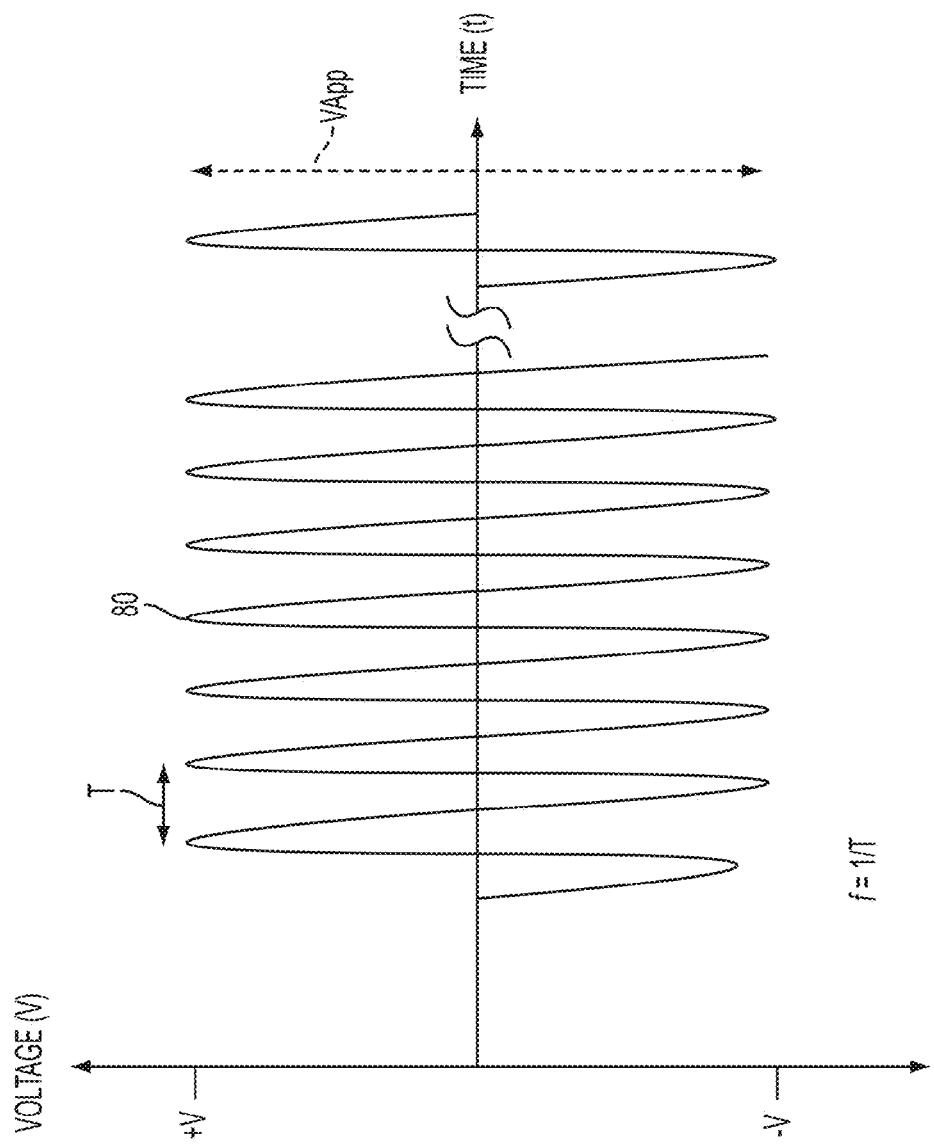
FIG. 5 is a graphical representation of an AC waveform that may be applied to undesirable tissue according to certain embodiments described herein.

FIG. 5 is a graphical representation of an AC waveform 80 generated by energy source 14 according to certain embodiments as described herein. Time (t) is shown along the horizontal axis and voltage (VAC) is shown along the vertical axis. The AC waveform 80 has a fundamental frequency f, and peak-to-peak voltage amplitude ($VA_{pp}$). In various embodiments, the AC waveform 80 may have a fundamental frequency f in the range of about 330 KHz to about 900 KHz, and peak-to-peak voltage amplitude ($VA_{pp}$) in the range of about 200 VAC to about 12,000 VAC. In other embodiments, the AC waveform 80 may have a fundamental frequency f in the range of about 400 KHz to about 500 KHz and peak-to-peak amplitude voltage ($VA_{pp}$) in the range of about 5,000 VAC to about 12,000 VAC. In one embodiment, the AC waveform 80 may have a fundamental frequency f of 500 KHz, and peak-to-peak voltage amplitude ($VA_{pp}$) of 12,000 VAC.

The energy source 14 may be configured to generate and deliver AC waveform 80 in pulses to treat substantial volumes of undesirable tissue in a treatment region with no or minimal thermal damage to surrounding tissue. Each pulse may have a duration $T_w$ delivered at a pulse period $T_1$ or a pulse frequency $f_1=1/T_1$. A timing circuit may be coupled to the output of the energy source 14 to generate electric pulses. The timing circuit may comprise one or more suitable switching elements to produce the electric pulses.

The energy source 14 may be configured to generate and deliver AC waveform 80 in several bursts, each burst including several pulses. A treatment regimen may comprise several bursts spaced apart by sufficient time $T_b$ to allow the temperature of the treated tissue to remain below a maximum temperature. The bursts may be delivered at a burst period T2 or a burst frequency f2=1/T2. Both pulse and burst frequencies may be varied within a particular treatment regimen to effectively treat target tissue while maintaining treated tissue temperature below a maximum temperature.

Figure 6:
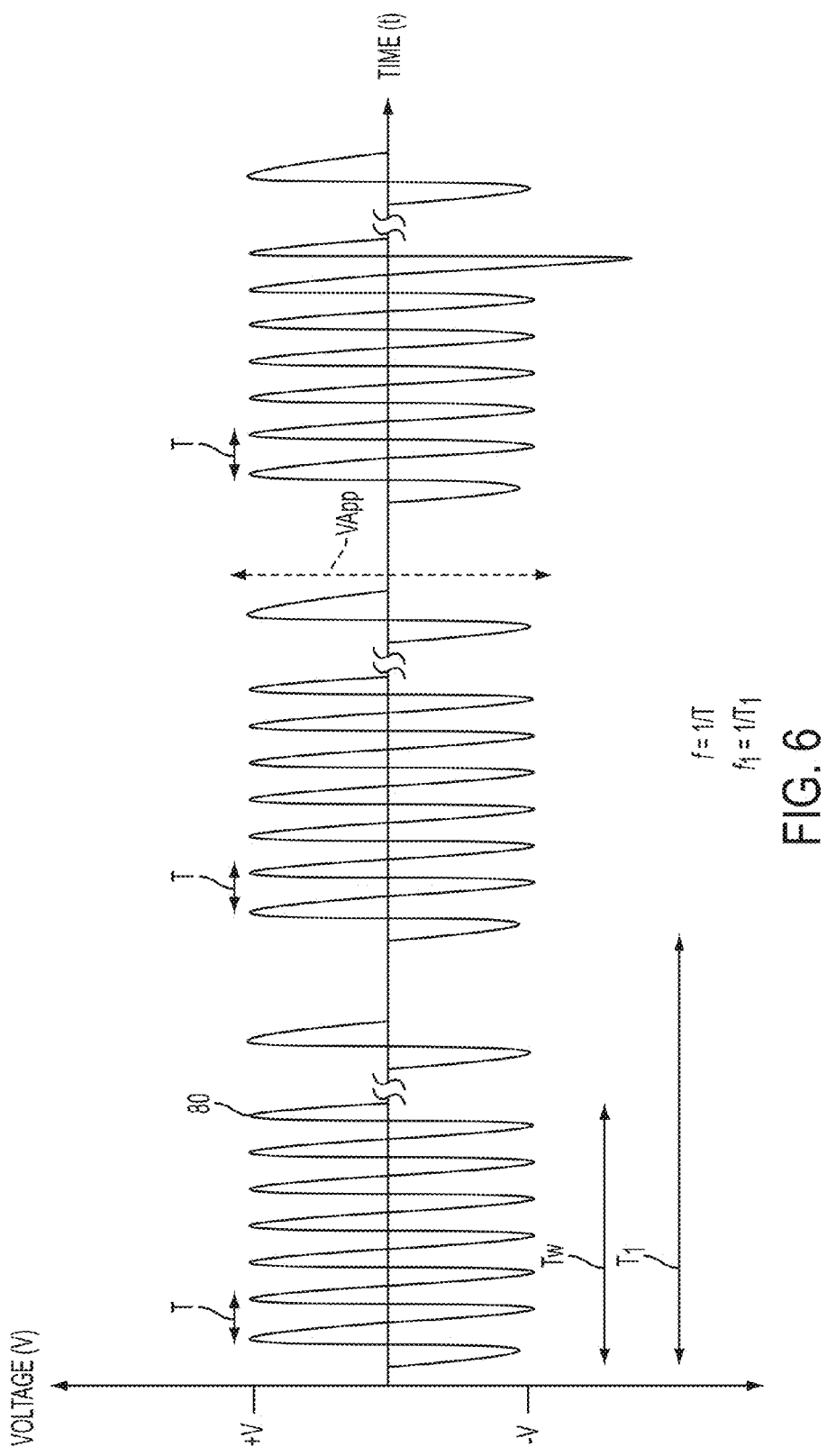
FIG. 6 is a graphical representation of a series of electrical pulses of the AC waveform of FIG. 5 that may be applied to undesirable tissue according to certain embodiments described herein.

FIG. 6 is a graphical representation of a burst of electrical pulses of AC waveform 80 generated and delivered by energy source 14. Time (t) is shown along the horizontal axis and voltage (VAC) is shown along the vertical axis. Waveform 80 has a fundamental frequency f, and a voltage peak-to-peak amplitude ($VA_{pp}$). In this exemplary embodiment, the burst includes three pulses. Each pulse has a duration $T_w$ delivered at a pulse period $T_1$ or a pulse frequency $f_1=1/T_1$. One of ordinary skill in the art will appreciate that the total energy delivered by each burst to the tissue can be varied by changing the voltage peak-to-peak amplitude ($VA_{pp}$), and/or the fundamental frequency f, the pulse width $T_w$, and/or the pulse frequency $f_1$.

In various embodiments, each pulse may have pulse duration $T_w$ in the range of about 5 microseconds to about 100 microseconds. In other embodiments, each pulse may have pulse duration $T_w$ in the range of about 10 microseconds to about 50 microseconds. In one embodiment, each pulse may have pulse duration $T_w$ of 20 microseconds. In various embodiments, the pulses may be delivered at pulse frequency $f_1$ in the range of about 1 Hz to about 500 Hz. In certain embodiments, pulse frequency $f_1$ may be in the range of about 1 Hz to about 100 Hz. In one embodiment, pulse frequency $f_1$ may be for example 4 Hz.

Figure 7:
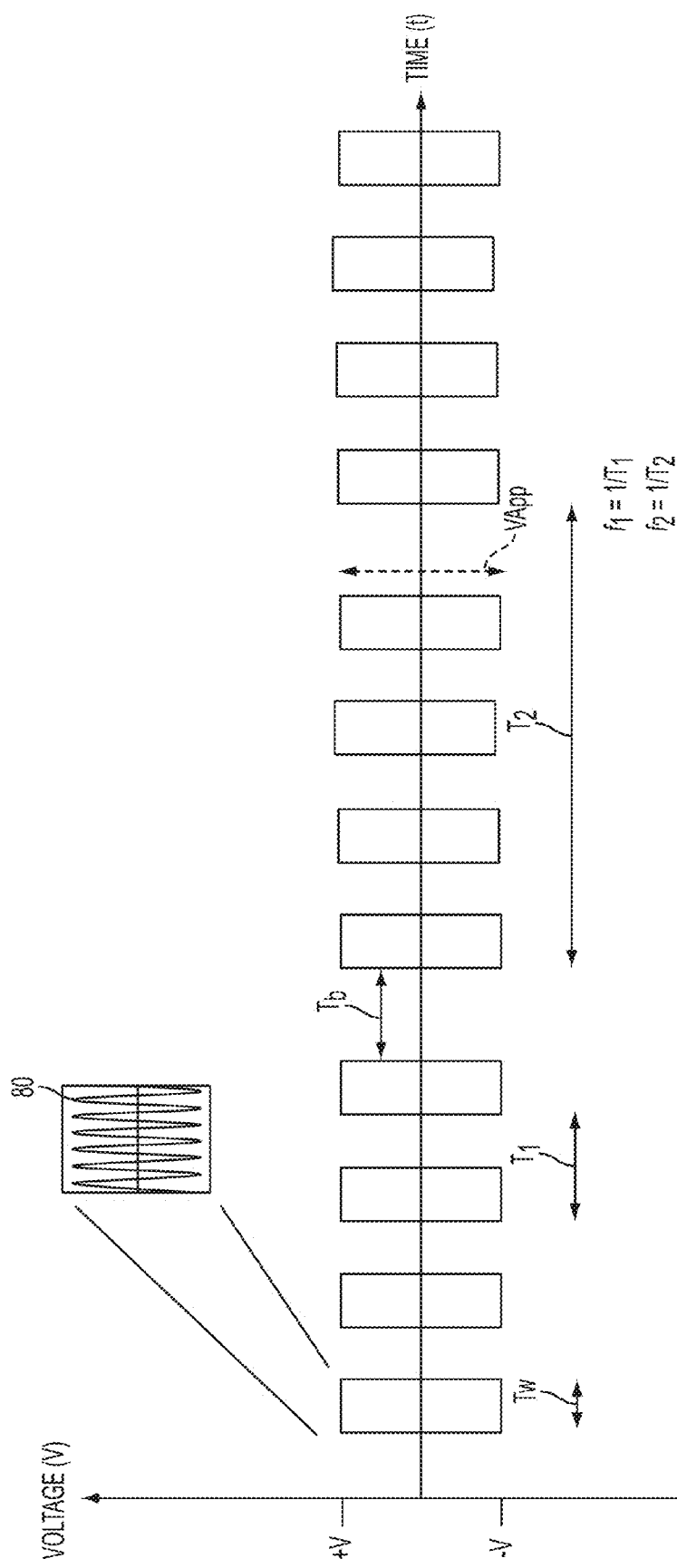
FIG. 7 is a graphical representation of multiple bursts of pulses of the AC waveform of FIG. 5 that may be applied to undesirable tissue according to certain embodiments described herein.

FIG. 7 is a graphical representation of multiple bursts of electrical pulses generated and delivered by energy source 14. Time (t) is shown along the horizontal axis and voltage (VAC) is shown along the vertical axis. In this exemplary embodiment, energy source 14 generates and delivers waveform 80 in three bursts. Each burst includes four pulses. Each pulse has a duration $T_w$ delivered at a pulse period T or a pulse frequency $f_1=1/T_1$. In addition, the bursts are spaced apart by sufficient time $T_b$ to allow the temperature of the treated tissue to remain below a maximum temperature. The bursts repeat at a burst frequency $f_2=1/T_2$.

In various embodiments, the bursts may repeat at a burst frequency $f_2$ in the range of about 0.02 Hz to about 500 Hz. In certain embodiments, burst frequency $f_2$ may be in the range of about 1 Hz to about 100 Hz. The number of bursts generated and delivered in a treatment regimen may also be varied to maintain tissue temperature below a maximum temperature. The number of bursts may be in the range of about 1 to about 100 bursts. In certain embodiments, the number of bursts may be in the range of about 5 to about 50 bursts.

Figure 8:
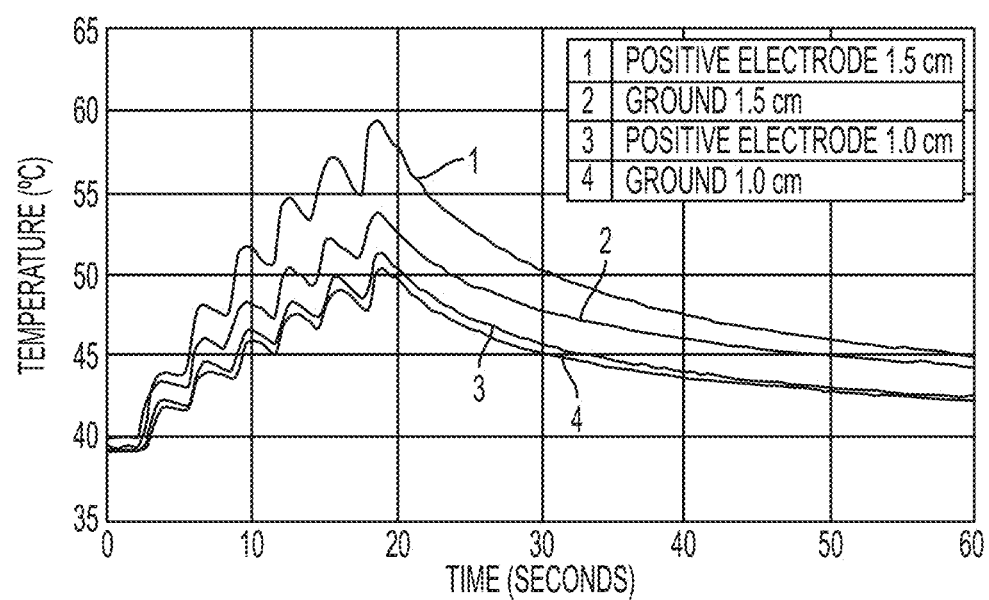
FIG. 8 is a graphical representation of electrode temperature during a series of electrical pulses that may be applied to undesirable tissue according to certain embodiments described herein.

Without wishing to be bound to any particular theory, in one aspect, temperature may be related to distance between electrodes. As shown in FIG. 8, an electrode spacing of 1.5 cm generated a maximum temperature of about 51° C. at the positive electrode and an electrode spacing of 1.0 cm generated a maximum temperature of about 59° C. at the positive electrode. As shown in FIG. 8, the temperature increases as the distance between the electrodes decreases. Temperature is also related to the total energy delivered to the tissue by electrosurgical system 10. During a particular treatment regimen, the various parameters of waveform 80 may be varied to ensure an effective treatment without undesirable overheating of the treated tissue.

In various embodiments, electrosurgical system 10 may treat and/or kill cells in undesirable tissue with no or minimal muscle contractions in a treated patient. It is well known that neural and muscle cells are electrically excitable, i.e. they can be stimulated by electric current. It is believed that sensitivity of the nerve and muscle cells to electric field is due to the voltage-gated ion channels present in their cell membranes. In patients, such stimulation may cause acute pain, muscle spasms, and even cardiac arrest. Typically, the sensitivity to electrical stimulation decreases with increasing frequency. Furthermore, it is also believed that neural and muscle cells are more sensitive to direct current. To minimize the effects of muscle and neural stimulation, electrosurgical system 10 may be configured to generate and deliver electric pulses of a biphasic AC waveform operating at a high fundamental frequency f such as in the range of about 330 KHz to about 900 KHz and peak-to-peak voltage amplitude ($VA_{pp}$) of about 200 VAC to about 12,000 VAC.

In various embodiments, a patient may be treated with electrosurgical system 10 without administering a paralytic agent. A paralytic agent is generally administered to reduce skeletal muscle contractions and cardiac events when a patient is treated with monophasic pulses.

Figure 9:
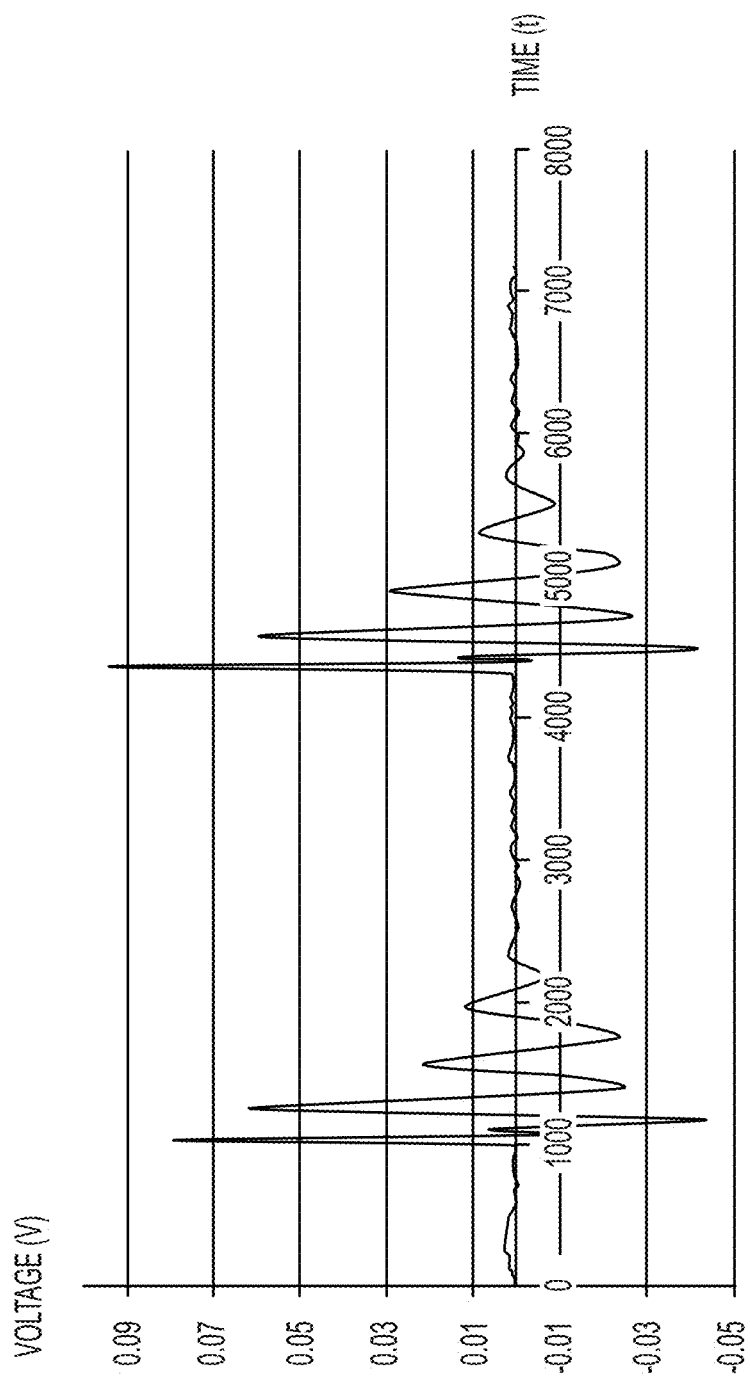
FIG. 9 is a graphical representation of a porcine model's muscle electrical activity in response to DC monophasic pulses.
Figure 10:
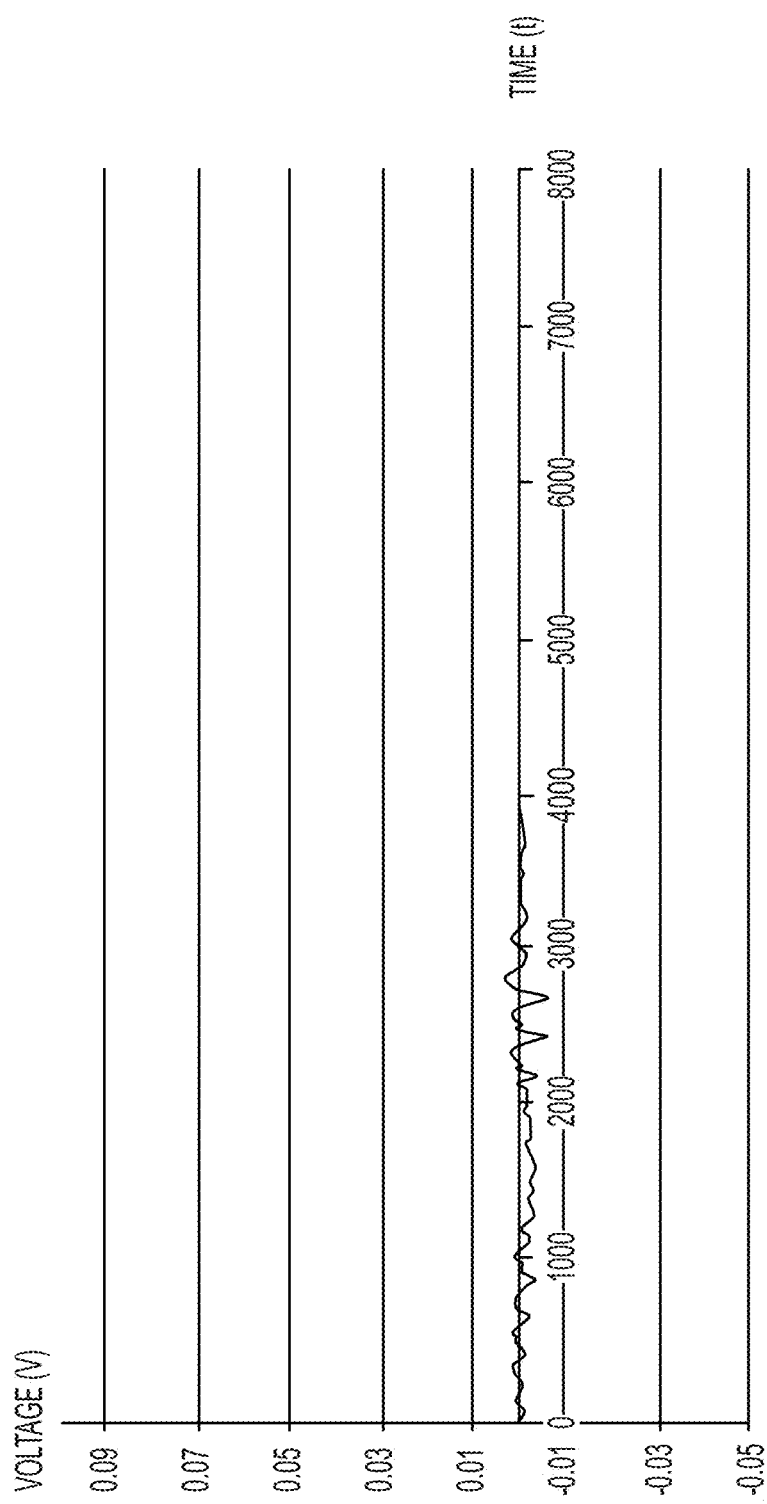
FIG. 10 is a graphical representation of a porcine model's muscle electrical activity in response to pulses of a biphasic AC waveform according to certain embodiments described herein.

FIGS. 9 and 10 are graphical representations of the severity of muscle contractions in a porcine model treated with monophasic pulses, in FIG. 9, and treated with electrosurgical system 10, in FIG. 10. Time (t) is shown along the horizontal axis and voltage (V) is shown along the vertical axis. Each treatment was delivered percutaneously via 2 needles spaced 1.5 cm apart in a porcine liver in absence of a paralytic agent. A standard BIOPAC system, readily available from BIOPAC Systems Inc. at Goleta, Calif., was utilized to record the change in muscle electrical activity in response to each treatment. FIG. 9 illustrates the severity of muscle contractions upon administration of two monophasic bursts. In comparison, FIG. 10 illustrates the severity of muscle contractions upon administration of two bursts generated and delivered by electrosurgical system 10. In this example, electrosurgical system 10 was configured to generate and deliver two bursts of an AC waveform operating at a fundamental frequency f of 500 KHz. Changes in voltage amplitude of each recording correspond to changes in muscle electrical activity. As evident by comparing FIGS. 9 and 10, the severity of muscle contractions, in the absence of a paralytic agent, is several orders of magnitude higher in the case of monophasic pulses.

Referring to FIG. 1, the energy source 14 may include a variable voltage power supply, a capacitor charged by the variable voltage power supply, and a switching amplifier which receives energy from the capacitor. The switching amplifier may be configured to output pulses of a biphasic radio frequency (RF) waveform capable of treating tissue by inducing non-thermal cell death in the tissue with no or minimal muscle contractions in a patient during treatment of the tissue.

The switching amplifier is a full bridge amplifier having a first phase of operation and a second phase of operation. The full bridge amplifier may be configured to output a positive voltage during the first phase of operation, and a negative voltage during the second phase of operation. Furthermore, the full bridge amplifier may be configured to alternate between the first and second phases of operation. The full bridge amplifier may include four switching legs. Each switching leg may have at least one switching element, and at least one drive circuit to control the at least one switching element. In certain embodiments, the energy source 14 may further include a drive logic to drive the drive circuits of at least two of the switching legs simultaneously during the first phase of operation, and to drive the drive circuits of at least two other switching legs simultaneously during the second phase of operation.

The energy source 14 may further include an isolating transformer having an energy input side and an energy output side. The energy input side may be configured to receive energy from the switching amplifier. The isolating transformer may be configured to minimize induction of low frequency energy from the energy input side to the energy output side. In at least one embodiment, the energy source 14 may further include a blocking capacitor configured to remove low frequency energy from the output of the switching amplifier.

Figure 11:
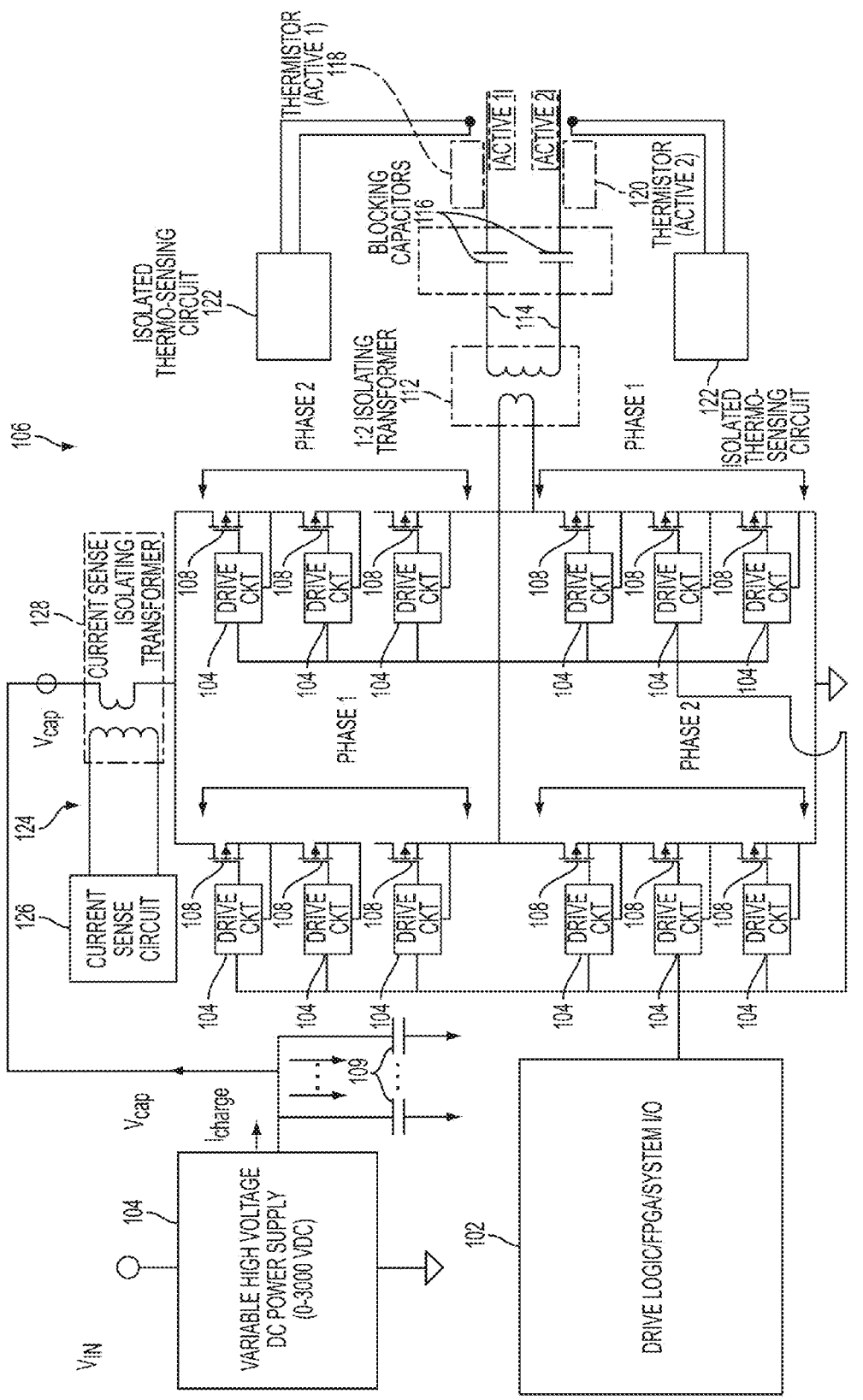
FIG. 11 is a circuit block diagram of an electrosurgical system according to certain embodiments described herein.

In various embodiments, energy source 14 may comprise a configuration as illustrated in FIG. 11, energy source 14 may include a system Input/Output (I/O) board 102, a variable voltage power supply 104, and a switching amplifier 106. The power supply 104 may be a high voltage direct current (DC) power supply with voltage amplitude in the range of about 0 VDC to about 3000 VDC. Energy source 14 may further include a system Input/Output (I/O) board 102, which controls the output of the power supply 104. A computer interface may be used to interact with the system I/O board 102 to set the amount of DC voltage output of the power supply 104.

In various embodiments, power supply 104 may charge several capacitors 109. In certain embodiments, capacitors 109 are configured to store large amounts of energy. Capacitors 109 suitable for such purpose include large bank, high quality, and high pulse current metalized polypropylene capacitors. Capacitors 109 may be charged by power supply 104 during the "OFF" time of the switching amplifier 106. Upon switching the switching amplifier 106 to the "ON" position, capacitors 109 may discharge the energy stored within into the switching amplifier 106.

In certain embodiments, as illustrated in FIG. 11, the switching amplifier 106 may be configured as a full bridge amplifier. In at least one embodiment, the switching amplifier 106 may be configured as a class D full bridge amplifier. The switching amplifier 106 may include a number of switching legs 111. In at least one embodiment, as illustrated in FIG. 11, the switching amplifier may include four switching legs 111. Each switching leg 111 may include power Biopolar Field Effect Transistors (BiFETs) 108, and associated drive circuits 110. By way of example, as illustrated in FIG. 11, each switching leg 111 may include three power BiFETs 108, and associated drive circuits 110. In certain embodiments, to be able to withstand high-voltage stress from power supply 104, the power BiFETs 108 of each switching leg 111 may be configured in series. That said, other configurations such as parallel should not be excluded from the scope of the present disclosure. In certain embodiments, switching leg 111 may turn ON simultaneously in a Class D operation to efficiently transfer the energy from the capacitors 109, charged by the power supply 104, into output circuitry.

In certain embodiments, as illustrated in FIG. 11, the switching amplifier 106 is configured with a first phase of operation (phase 1) and a second phase of operation (phase 2). In certain embodiments, the switching amplifier 106 is configured to output positive voltage during phase 1 and negative voltage during phase 2. A driver logic 102 may be configured to operate each phase at the appropriate time. In certain embodiments, driver logic 102 is configured to alternate between phase 1 and phase 2.

In certain embodiments, Phase 1 is begun after charging the capacitors 109. During phase 1, a positive voltage may be produced on one side of an output transformer 112. Phase 2 is begun after Phase 1 is ended. During Phase 2, a negative voltage may be produced on the same side of the output transformer. In certain embodiments, an anti-overlap time between phase 1 and phase 2 ensures that there is no pass through current when phase 2 is begun. In most cases, the anti-overlap time is so small that it cannot be seen in the output waveform. An additional anti-overlap time may be applied before the repeat of the cycle. The output of the switching amplifier 106 is a switching, biphasic waveform.

In certain embodiments, the output transformer 112 may be an isolating transformer. In at least one embodiment, output transformer 112 may be a 1:2 isolating transformer capable of doubling the voltage of the output waveform. For example, if the capacitors 109 are charged to 3000 VDC, the output transformer 112 may increase the voltage of the output waveform to a 6000 V positive peak and a 6000 V negative peak. In certain embodiments, output transformer 112 may include primary 113 and secondary 115 windings that are isolated with double insulating material. The isolation of the primary windings 113 from the secondary windings 115 protects and isolates the secondary windings 115 from the DC voltage characteristics contained within the primary windings 113 of the output transformer 112. Such isolation may aid in eliminating low frequency energy.

In certain embodiments, as illustrated in FIG. 11, each leg 114 of the output transformer 112 is connected to a blocking capacitor 116. The blocking capacitors 116 may be configured to pass high frequency energy, and block low frequency energy to ensure that the energy source 14 delivers high frequency biphasic current to treated tissue.

In various embodiments, energy source 14 may include thermistors for monitoring tissue temperature. As shown in FIG. 11, a first thermistor 118 is employed at a positive lead and a second thermistor 120 is employed at a negative lead. An isolated, thermal sensing circuit 122 may record temperature and report this information to the system I/O board 102. The information can then be processed and the output of energy source 14 adjusted to maintain an appropriate temperature.

In Various embodiments, energy source 14 may comprise current sensors to monitor the current flowing through the switching amplifier 106. As illustrated in FIG. 11, current sensor 124 may comprise a current sensing circuit 126, and a current sensing isolating transformer 128. Current sensors protect BiFETs 108 of the switching amplifier 106 from power overload by terminating the system if operative current reaches excessive amounts.

The embodiments of the electrosurgical systems described herein may be introduced inside a patient using minimally invasive or open surgical techniques. In some instances, it may be advantageous to introduce the electrosurgical systems inside the patient using a combination of minimally invasive and open surgical techniques. Minimally invasive techniques may provide more accurate and effective access to the treatment region for diagnostic and treatment procedures. To reach internal treatment regions within the patient, the electrosurgical systems described herein may be inserted through natural openings of the body such as the mouth, anus, and/or vagina, for example. Minimally invasive procedures performed by the introduction of various medical devices into the patient through a natural opening of the patient are known in the art as NOTES™ procedures. Surgical devices, such as an electrosurgical systems, may be introduced to the treatment region through the channels of the endoscope to perform key surgical activities (KSA), including, for example, electrosurgical of tissues using irreversible electroporation energy. Some portions of the electrosurgical systems may be introduced to the tissue treatment region percutaneously or through small—keyhole—incisions.

Endoscopic minimally invasive surgical and diagnostic medical procedures are used to evaluate and treat internal organs by inserting a small tube into the body. The endoscope may have a rigid or a flexible tube. A flexible endoscope may be introduced either through a natural body opening (e.g., mouth, anus, and/or vagina). A rigid endoscope may be introduced via trocar through a relatively small—keyhole—incision incisions (usually 0.5 cm to 1.5 cm). The endoscope can be used to observe surface conditions of internal organs, including abnormal or diseased tissue such as lesions and other surface conditions and capture images for visual inspection and photography. The endoscope may be adapted and configured with channels for introducing medical instruments to the treatment region for taking biopsies, retrieving foreign objects, and/or performing surgical procedures.

Once an electrosurgical system is inserted in the human body internal organs may be reached using trans-organ or translumenal surgical procedures. The electrosurgical system may be advanced to the treatment site using endoscopic translumenal access techniques to perforate a lumen, and then, advance the electrosurgical system and the endoscope into the peritoneal cavity. Translumenal access procedures for perforating a lumen wall, inserting, and advancing an endoscope therethrough, and pneumoperitoneum devices for insufflating the peritoneal cavity and closing or suturing the perforated lumen wall are well known. During a translumenal access procedure, a puncture must be formed in the stomach wall or in the gastrointestinal tract to access the peritoneal cavity. One device often used to form such a puncture is a needle knife which is inserted through the channel of the endoscope, and which utilizes energy to penetrate through the tissue. A guidewire is then feed through the endoscope and is passed through the puncture in the stomach wall and into the peritoneal cavity. The needle knife is removed, leaving the guidewire as a placeholder. A balloon catheter is then passed over the guidewire and through the channel of the endoscope to position the balloon within the opening in the stomach wall. The balloon can then be inflated to increase the size of the opening, thereby enabling the endoscope to push against the rear of the balloon and to be feed through the opening and into the peritoneal cavity. Once the endoscope is positioned within the peritoneal cavity, numerous procedures can be performed through the channel of the endoscope.

The endoscope may be connected to a video camera (single chip or multiple chips) and may be attached to a fiber-optic cable system connected to a "cold" light source (halogen or xenon), to illuminate the operative field. The video camera provides a direct line-of-sight view of the treatment region. If working in the abdomen, the abdomen may be insufflated with carbon dioxide ($CO_2$) gas to create a working and viewing space. The abdomen is essentially blown up like a balloon (insufflated), elevating the abdominal wall above the internal organs like a dome. $CO_2$ gas is used because it is common to the human body and can be removed by the respiratory system if it is absorbed through tissue.

Once the electrosurgical systems are located at the target site, the diseased tissue may be electrically ablated or destroyed using the various embodiments of electrodes discussed herein. The placement and location of the electrodes can be important for effective and efficient electrosurgical therapy. For example, the electrodes may be positioned proximal to a treatment region (e.g., target site or worksite) either endoscopically or transcutaneously (percutaneously). In some implementations, it may be necessary to introduce the electrodes inside the patient using a combination of endoscopic, transcutaneous, and/or open techniques. The electrodes may be introduced to the tissue treatment region through a channel of the endoscope, an overtube, or a trocar and, in some implementations, may be introduced through percutaneously or through small—keyhole—incisions.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

The various embodiments described herein may be better understood when read in conjunction with the following representative examples. The following examples are included for purposes of illustration and not limitation.

Figure 12:
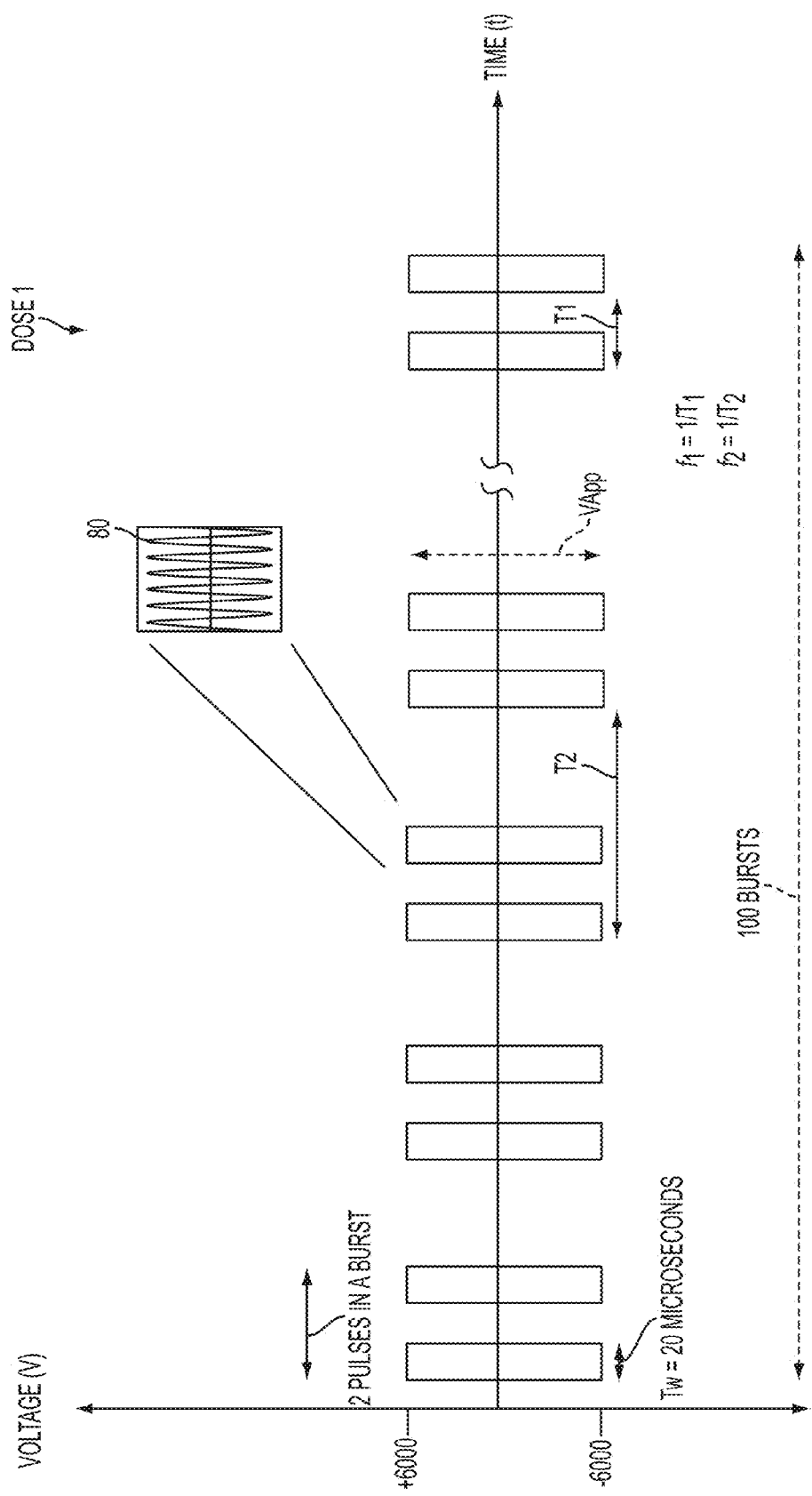
FIG. 12 is a graphical representation of a treatment regimen generated and delivered by an electrosurgical system according to certain embodiments described herein.
Figure 13:
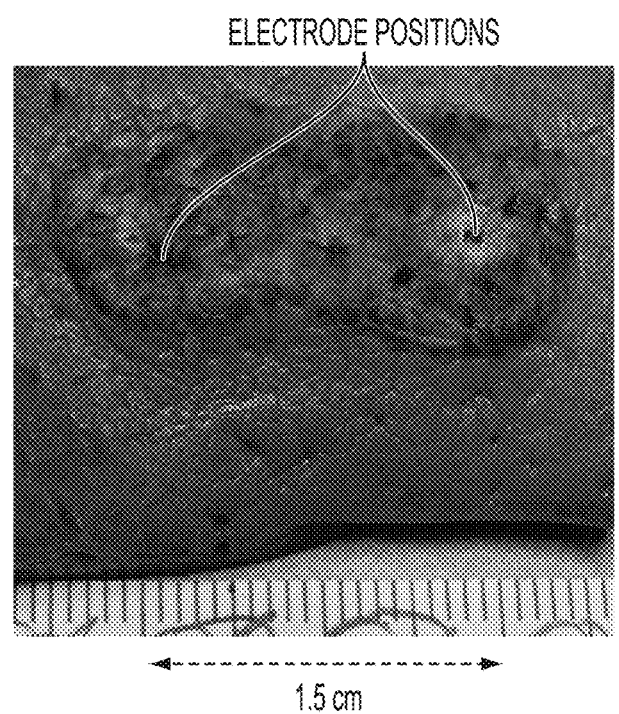
FIG. 13 is a photograph of a porcine liver after receiving electrical pulses that may be applied to undesirable tissue according to certain embodiments described herein.

An electrosurgical system comprising a first and second electrodes coupled to an energy source comprising an AC waveform generator, and a temperature sensor according to certain embodiments was used to deliver an AC waveform 80 in a series of electrical bursts ex vivo to healthy porcine liver (Dose 1). As illustrated in FIG. 12, Dose 1 includes 100 bursts. Each burst has a burst period $T_2$ or a burst frequency, $f2=1/T_2$, of 0.5 Hz. Each burst includes 2 pulses. Each pulse has a duration $T_w$ of 20 microseconds delivered at a pulse period $T_1$ or a pulse frequency, $f_1=1/T_1$, of 4 Hz. The AC waveform 80 operates at fundamental frequency of 500 KHz and has peak-to-peak voltage amplitude ($VA_{pp}$) of 12,000 V. The temperature was monitored using the temperature sensor illustrated in FIG. 4, and was maintained below or equal to 60° C. FIG. 13 includes a photograph of porcine liver after the treatment with Dose 1. In this instance, the first and second electrodes were positioned 1.5 cm apart.

Figure 14:
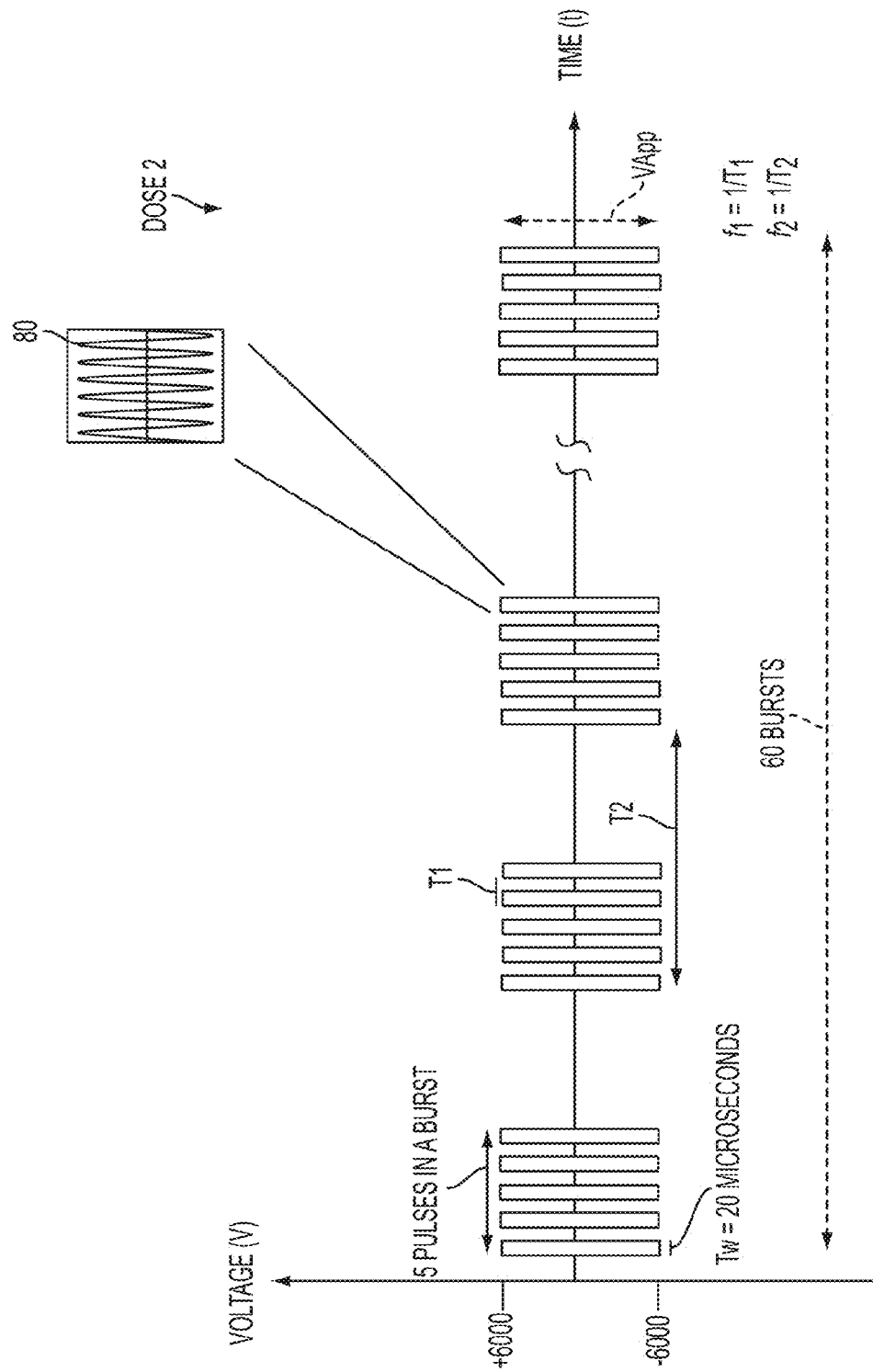
FIG. 14 is a graphical representation of a treatment regimen generated and delivered by an electrosurgical system according to certain embodiments described herein.
Figure 15:
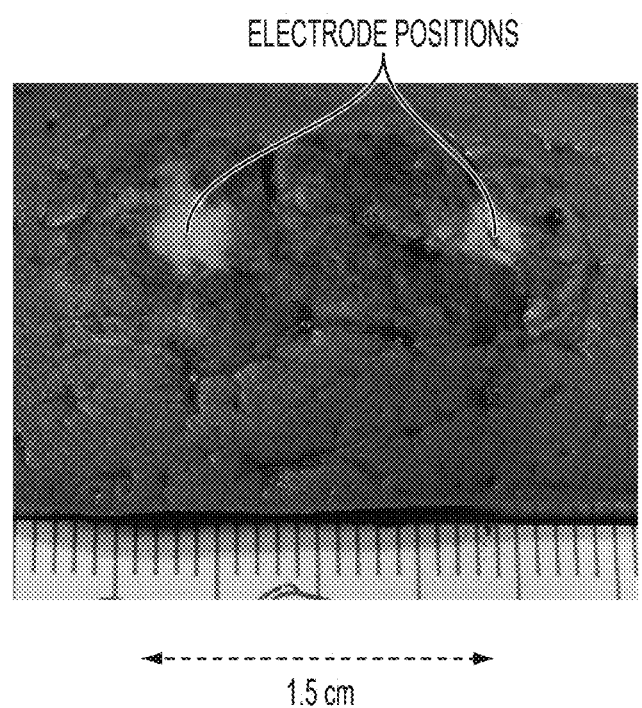
FIG. 15 is a photograph of a porcine liver after receiving electrical pulses that may be applied to undesirable tissue according to certain embodiments described herein.

An electrosurgical system comprising a first and second electrodes coupled to an energy source comprising an AC waveform generator, and a temperature sensor according to certain embodiments was used to deliver an AC waveform 80 in a series of electrical bursts ex vivo to healthy porcine liver (Dose 2). As illustrated in FIG. 14, Dose 2 may include 60 bursts. Each burst has a burst period $T_2$ or a burst frequency, $f2=1/T_2$, of 0.2 Hz. Each burst includes 5 pulses. Each pulse has a duration $T_w$ of 20 microseconds delivered at a pulse period $T_1$ or a pulse frequency, $f_1=1/T_1$, of 4 Hz. The AC waveform 80 operates at fundamental frequency of 500 KHz and has peak-to-peak voltage amplitude ($VA_{pp}$) of 12,000 V. The temperature was monitored using the temperature sensor illustrated in FIG. 4 and was maintained below or equal to 60° C. FIG. 15 includes a photograph of porcine liver after the treatment Dose 2. In this instance, the first and second electrodes were positioned 1.5 cm apart.

Figure 16:
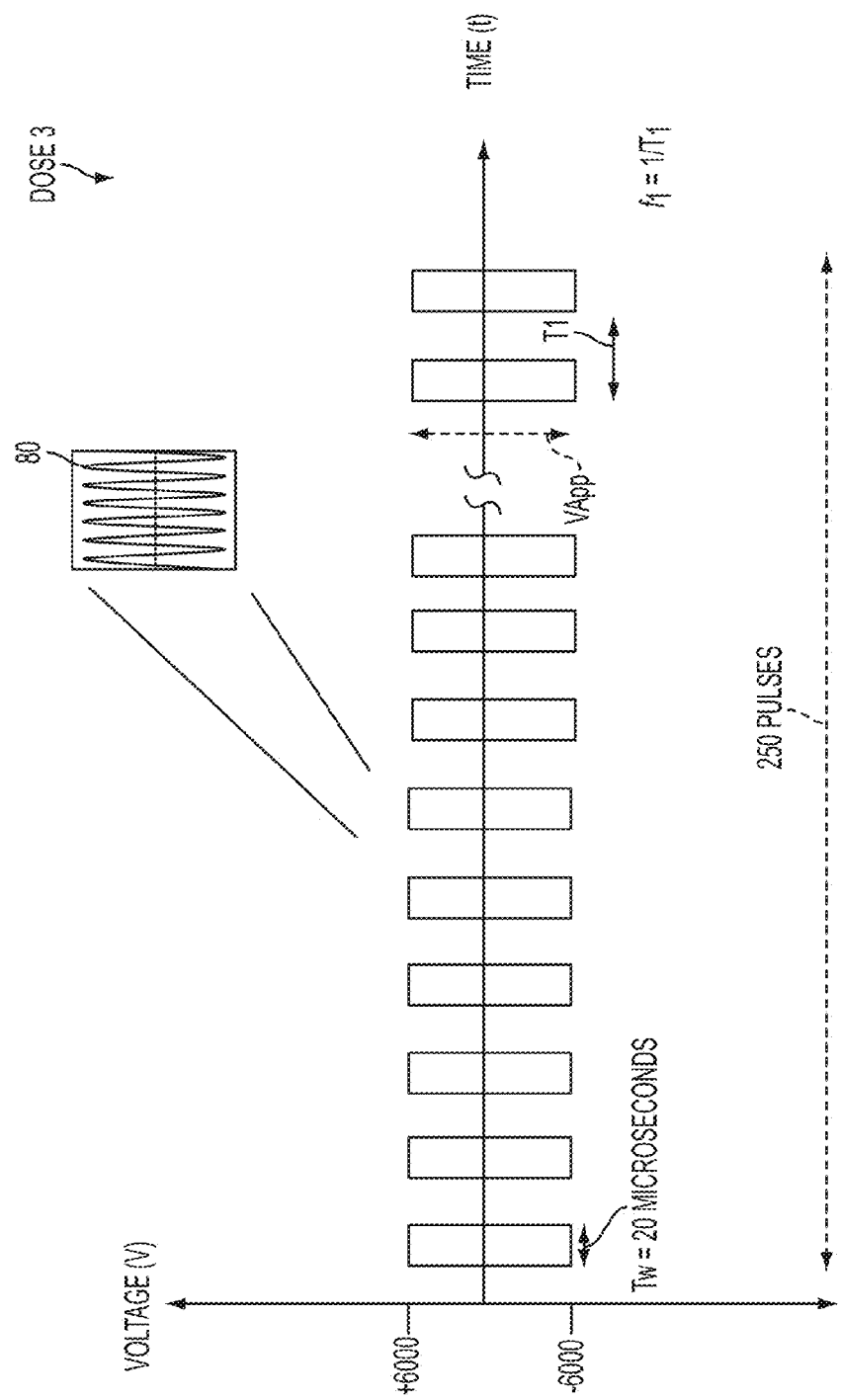
FIG. 16 is a graphical representation of a treatment regimen generated and delivered by an electrosurgical system according to certain embodiments described herein.
Figure 17:
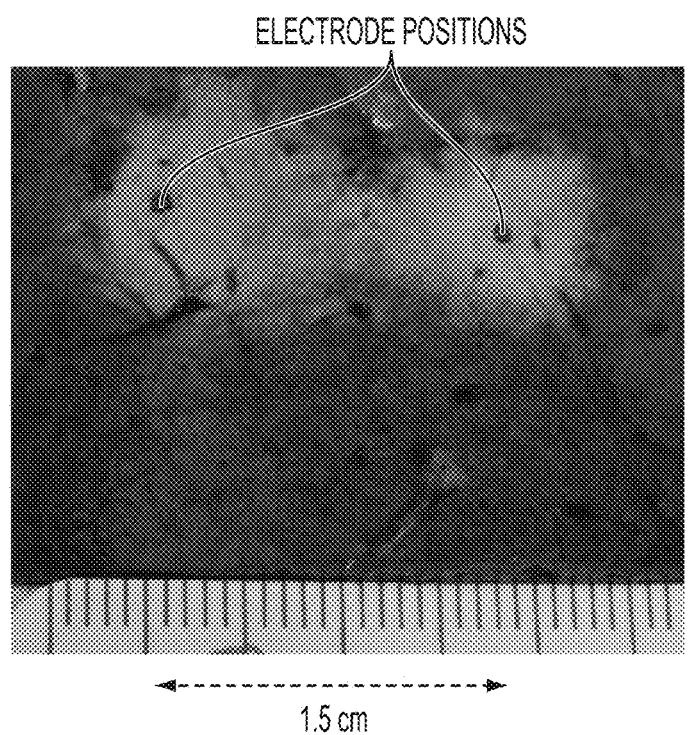
FIG. 17 is a photograph of a porcine liver after receiving electrical pulses that may be applied to undesirable tissue according to certain embodiments described herein.

An electrosurgical system comprising a first and second electrodes coupled to an energy source comprising an AC waveform generator, and a temperature sensor according to certain embodiments was used to deliver an AC waveform 80 in a series of electrical pulses ex vivo to healthy porcine liver (Dose 3). As illustrated in FIG. 16, Dose 3 includes 250 pulses. Each pulse has a duration $T_w$ of 20 microseconds delivered at a pulse period $T_1$ or a pulse frequency, $f_1=1/T_1$, of 500 Hz. The AC waveform 80 operates at fundamental frequency of 500 KHz and has peak-to-peak voltage amplitude ($VA_{pp}$) of 12,000 V. The temperature was monitored using the temperature sensor illustrated in FIG. 4 and was maintained below or equal to 60° C. FIG. 17 includes a photograph of porcine liver after the treatment with Dose 3. In this instance, the first and second electrodes were positioned 1.5 cm apart.

The devices disclosed herein can be designed to be disposed of after a single use, or they can be designed to be used multiple times. In either case, however, the device may be reconditioned for reuse after at least one use. Reconditioning can include any combination of the steps of disassembly of the device, followed by cleaning or replacement of particular elements, and subsequent reassembly. In particular, the device may be disassembled, and any number of particular elements or components of the device may be selectively replaced or removed in any combination. Upon cleaning and/or replacement of particular components, the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Preferably, the various embodiments described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam, autoclaving, soaking in sterilization liquid, or other known processes.

Although various embodiments have been described herein, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An energy source for use with an electrosurgical system, comprising:
    a variable voltage power supply;
    at least one capacitor charged by the variable voltage power supply; and
    a switching amplifier receiving energy from the at least one capacitor, wherein the switching amplifier is configured to output pulses of a biphasic radio frequency (RF) waveform, wherein the pulses are capable of treating targeted tissue of a patient by inducing non-thermal cell death in the targeted tissue, and wherein the pulses cause no or minimal contraction in muscular tissue of the patient within reach of the biphasic RF waveform during treatment of the targeted tissue.

2. The energy source of claim 1, wherein the switching amplifier is a full bridge amplifier having a first phase of operation and a second phase of operation, wherein the full bridge amplifier is configured to output a positive voltage during the first phase of operation, and a negative voltage during the second phase of operation, and wherein the full bridge amplifier is configured to alternate between the first phase of operation and the second phase of operation.

3. The energy source of claim 1, wherein the switching amplifier includes at least four switching legs, and wherein each switching leg comprises at least one switching element and at least one drive circuit to control the at least one switching element.

4. The energy source of claim 3, further comprising a drive logic to drive the drive circuits of at least two of the switching legs simultaneously during a first phase of operation and to drive the drive circuits of at least two other switching legs simultaneously during a second phase of operation.

5. The energy source of claim 1, further comprising an isolating transformer having an energy input side and an energy output side, wherein the energy input side receives energy from the switching amplifier, and wherein the isolating transformer is configured to minimize induction of low frequency energy from the energy input side to the energy output side.

6. The energy source of claim 1, further comprising at least one blocking capacitor configured to remove low frequency energy from the output of the switching amplifier.

7. The energy source of claim 1, further comprising a current monitoring member to ensure current amounts delivered to the switching amplifier remain below a predetermined maximum.

8. The energy source of claim 1, wherein the biphasic RF waveform operates at a fundamental frequency of about 330 KHz to about 900 KHz and comprises a peak-to-peak voltage amplitude of about 200 VAC to about 12,000 VAC.

9. The energy source of claim 1, wherein each pulse comprises a pulse duration of about 5 µs to about 100 µs delivered at a pulse frequency of about 1 Hz to about 500 Hz.

10. The energy source of claim 1, wherein the switching amplifier is configured to output the pulses in a plurality of bursts, wherein each burst comprises a plurality of pulses, and wherein each burst is separated by a time period sufficient to maintain the targeted tissue below a maximum temperature.

11. The energy source of claim 10, wherein the switching amplifier is configured to repeat the plurality of bursts at a burst frequency of about 0.02 Hz to about 500 Hz.

12. The energy source of claim 1, wherein the biphasic radio frequency (RF) waveform comprises a first phase and a second phase separated by an anti-overlap time.

13. An energy source for use with an electrosurgical system, comprising:
    a variable voltage power supply;
    a plurality of capacitors electrically coupled to the power supply; and
    a switching amplifier electrically coupled to the plurality of capacitors, wherein the switching amplifier is configured to output pulses of a biphasic alternating current (AC) waveform, wherein the pulses are operative to treat targeted tissue by inducing a change in voltage potential across cell membranes of the targeted tissue, and wherein the pulses cause no or minimal contraction in muscular tissue of the targeted tissue during treatment of the targeted tissue.

14. The energy source of claim 13, wherein the switching amplifier includes a plurality of switching legs, wherein each switching leg comprises at least one bipolar field effect transistor (BiFET), and wherein each BiFET is associated with a drive circuit to control its respective BiFET.

15. The energy source of claim 14, further comprising a drive logic configured to drive the drive circuits of at least two switching legs simultaneously during a first phase of operation and to drive the drive circuits of at least two other switching legs simultaneously during a second phase of operation.

16. The energy source of claim 13, further comprising an isolating transformer comprising an energy input side and an energy output side, wherein the isolating transformer is configured to increase a first voltage associated with a biphasic AC waveform received from the switching amplifier at the energy input side to a second voltage at the energy output side.

17. The energy source of claim 13, further comprising at least one blocking capacitor configured to block low frequency energy such that only high frequency energy is outputted to the targeted tissue.

18. The energy source of claim 13, further comprising:
an input-output board operable to control energy output by the power supply;
at least one thermistor; and
at least one thermal sensing circuit operable to report a temperature to the input-output board, wherein the input-output board is operative to adjust the energy output to maintain a predetermined temperature.

19. The energy source of claim 13, wherein the biphasic AC waveform comprises a first phase and a second phase separated by an anti-overlap time.

20. An energy source for use with an electrosurgical system, comprising:
a power supply;
one or more capacitors coupled to the power supply; and
a switching component coupled to the one or more capacitors, wherein the switching component is configured to output pulses of a biphasic waveform, and wherein the pulses are capable of treating undesired tissue by inducing a change in voltage potential across cell membranes of a plurality of cells in the undesired tissue to promote non-thermal cell death in the plurality of cells while causing no or minimal contraction in muscular tissue in electrical contact with the undesired tissue during treatment of the undesired tissue.

21. The energy source of claim 20, wherein the switching component comprises a first phase of operation and a second phase of operation, wherein the switching component is configured to output a positive voltage during the first phase of operation and a negative voltage during the second phase of operation, and wherein the switching component is configured to alternate between the first phase of operation and the second phase of operation.

22. The energy source of claim 20, wherein the switching component is configured to output the pulses of the biphasic waveform at a radio frequency.

23. The energy source of claim 20, wherein the biphasic waveform operates at a fundamental frequency of about 330 KHz to about 900 KHz and comprises a peak-to-peak voltage amplitude of about 200 VAC to about 12,000 VAC.

24. The energy source of claim 20, wherein the biphasic waveform comprises a first phase and a second phase separated by an anti-overlap time.

* * * * *